(12) United States Patent
Kotani et al.

(10) Patent No.: US 7,871,765 B2
(45) Date of Patent: Jan. 18, 2011

(54) COMPOSITION HAVING ANTITUMOR EFFECT

(75) Inventors: Hitoshi Kotani, Hyogo (JP); Yasufumi Kaneda, Osaka (JP); Hirokazu Kawano, Osaka (JP); Masayuki Fukumura, Osaka (JP); Masayuki Kurooka, Osaka (JP)

(73) Assignees: GenomIdea Inc., Osaka (JP); AnGesMG, Inc., Osaka (JP)

( * ) Notice: Subject to any disclaimer, the term of this patent is extended or adjusted under 35 U.S.C. 154(b) by 106 days.

(21) Appl. No.: 10/594,443

(22) PCT Filed: Mar. 31, 2005

(86) PCT No.: PCT/JP2005/006820

§ 371 (c)(1),
(2), (4) Date: Dec. 20, 2006

(87) PCT Pub. No.: WO2005/094878

PCT Pub. Date: Oct. 13, 2005

(65) Prior Publication Data

US 2008/0226674 A1    Sep. 18, 2008

(30) Foreign Application Priority Data

Mar. 31, 2004  (JP) ............... 2004-108599
Apr. 30, 2004  (JP) ............... 2004-136756
Feb. 21, 2005  (JP) ............... 2005-044639

(51) Int. Cl.
*C12Q 1/70*    (2006.01)

(52) U.S. Cl. ......................... 435/5; 435/7.23

(58) Field of Classification Search .............. None
See application file for complete search history.

(56) References Cited

FOREIGN PATENT DOCUMENTS

EP     1170363 A1    1/2002
EP     1420065 A1    5/2004
EP     1447451 A1    8/2004
JP     2001-286282 A  10/2001
JP     2001-302541 A  10/2001
JP     2002-065278 A   3/2002
WO     WO 94/21798    9/1994
WO     WO 98/50071   11/1998

OTHER PUBLICATIONS

Tsuyoshi Nakanishi et al., "Antigen-delivery system for CTL vaccine", Drug Delivery System, 1999, vol. 14, No. 6, pp. 459 to 469.
Palmer, J. C. et al., Non-infectious virus induces cytotoxic T Lymphocytes and binds to target cells to permit their lysis, Nature, 1977, vol. 269, pp. 595 to 597.
Fukami, Y. et al., Difference in Capacity of Sendai Virus Envelope Components to Induce Cytotoxic T Lymphocytes in Primary and Secondary Immune Responses, Infection and Immunity, 1979, vol. 26, No. 3, pp. 815 to 821.
Fujihara et al., "Intratumoral injection of inactivated Sendai virus particles elicits strong antitumor activity by enhancing local CXCL10 expression and systemic NK cell activation," *Cancer Immunol. Immunother.* 57, 73-84, 2008.
Kawaguchi et al., "Efficient eradication of hormone-resistant human prostate cancers by inactivated Sendai virus particle," *Int. J. Cancer* 124, 2478-87, 2009.
Kurooka & Kaneda, "Inactivated Sendai Virus Particles Eradicate Tumors by Inducing Immune Responses through Blocking Regulatory T Cells," *Cancer Res* 67, 227-236, 2007.

*Primary Examiner*—Stacy B Chen
(74) *Attorney, Agent, or Firm*—Banner & Witcoff, Ltd.

(57) ABSTRACT

The present invention is intended to provide a pharmaceutical composition for delivering a chemotherapeutic, preferably an anticancer drug, into cells or into a living organism, using a viral envelope vector, and provides a pharmaceutical composition comprising a chemotherapeutic encapsulated in, or used in combination with, a viral envelope vector having an adjuvanticity as an active ingredient. Thereby it is possible to introduce an anticancer drug encapsulated in a viral envelope vector directly into a tumor, with coadministration of another anticancer drug so as to induce tumor cell-specific antitumor immunity also thanks to the adjuvant action of HVJ-E, and hence to regress the tumor. The present invention also provides a pharmaceutical composition comprising a viral envelope vector and a chemotherapeutic as active ingredients.

2 Claims, 19 Drawing Sheets

US 7,871,765 B2

COMPOSITION HAVING ANTITUMOR EFFECT

This application is a National Stage application of co-pending PCT application PCT/JP2005/006820 filed Mar. 31, 2005, which was published on Oct. 13, 2005, and which claims the benefit of Japanese patent applications Serial No. 108599/2004 filed Mar. 31, 2004; 136756/2004 filed Apr. 30, 2004; and 044639/2005 filed Feb. 21, 2005.

TECHNICAL FIELD

The present invention relates to a vehicle for inducing antitumor immunity in a living organism. More specifically, the present invention relates to inducing more potent antitumor immunity by introducing a chemotherapeutic agent, preferably an anticancer drug, in combination with, or encapsulated in, a virus, specifically an inactivated virus, particularly an inactivated hemagglutinating virus of Japan (hereinafter also referred to as HVJ), into a solid tumor, and further systemically coadministering an anticancer drug. The present invention also relates to a pharmaceutical composition exhibiting antitumor action, which comprises a viral envelope and an anticancer drug.

BACKGROUND ART

In current cancer treatment, the cure rate is reportedly about 50%, and healing is generally often achieved by topical therapies such as surgical therapy and radiotherapy. In particular, in the treatment of solid cancers, the relative contribution of chemotherapy, which is a systemic therapy, to healing when it is used alone, is very low, and it is common practice to use it in combination with various other therapies.

In surgical therapy, all visceral cancers are operable; this therapy is considered to have already reached completion as a therapeutic approach, and no further improvement in cure rate is expected. As for radiotherapy, therapeutic results for the treatment of responsive visceral organs have become nearly constant, and no further improvement in cure rate is expected, as with surgical therapy.

Therefore, because these therapies are no longer likely to significantly improve the cancer cure rate from now on, the cancer cure rate cannot be increased from the current level of 50% to achieve cancer control unless a better chemotherapy is developed.

Anticancer drugs used for chemotherapy are intended to obtain cell-killing effects on cells of high growth potential such as cancer cells, and cause major damage to normal cells, particularly to myelocytes and other cells of high cell growth potential, resulting in a major burden on the patient. This is because the anticancer drug is delivered by systemic administration of an injection, so that the anticancer drug reaches not only cancer cells but also normal cells and kills normal cells to hamper the functioning of homeostasis.

However, at present, the efficacy rate of an anticancer drug administered alone is reported to be roughly about 30%; although it is hoped that advances in analytical research in genetic information of genome will enable the selection of appropriate anticancer drugs in the future, the currently available anticancer drug therapy is reported to produce a higher prevalence of side-effects compared with their efficacy.

This is because normal cells are damaged by the systemic administration of the anticancer drug. Hence, provided that a method is established of introducing an anticancer drug specifically to cancer tissue, and incorporating the agent into cancer cells, an ideal anticancer drug delivery system would be realized. Furthermore, if it is possible to encapsulate an anticancer drug into a vesicle, a therapy could be established that act selectively on target organs or cells with little influence on normal cells (side-effects). Additionally, this is considered to lead to a re-evaluation of anticancer drugs the development of which has been discontinued due to strong side-effects.

Additionally, therapeutic results for malignant tumors have recently been remarkably improved with the advances in multidisciplinary treatment centered on chemotherapy. In particular, in hematopoietic tumors such as leukemia and malignant lymphoma, healing is well expectable when these therapies are used in combination with hematopoietic stem cell transplantation and the like. However, no more than toxic effects of anticancer drugs, radiotherapy and the like are observed in some cases; there is a limitation in the eradication of tumor cells. Basic research and clinical observations have shown that the selective elimination of tumor cells by immune system is important. The immune system acts by recognizing proteins (peptides) and non-peptide antigens such as saccharides and lipids, whether the relevant organ is mucosal or non-mucosal. Upon entry of pathogen in the body, mainly monocytes migrate to the entry site and exhibit antigen-non-specific protective responses via phagocytosis and the like. Natural immunity against non-peptides such as saccharides and lipids and the like is first induced, helping the production of various factors concerning the elimination of pathogens. Subsequently, lymphocytes that recognize pathogenic peptides grow and differentiate; B lymphocytes differentiate into antibody-producing cells and T lymphocytes differentiate into helper T cells, cytotoxic T cells and the like, which control the immune system, thus inducing antigen-specific immune responses, i.e., what is called acquired immunity. There are two types of acquired immunity: humoral immunity, in which antibodies play the key role, and cellular immunity, in which T lymphocytes play the key role. Which is the prevalent type of immunity, whether cellular immunity or humoral immunity, depends on which is the prevalent subtype of helper T cells, whether Th1 or Th2. When the immune state is inclined to Th1-dominant, cellular immunity will prevail; when the immune state is inclined to Th2-dominant, humoral immunity will prevail. The two types of immunity occur in a mutual balance; these immune states rely on cytokines, which are humoral molecules secreted by various cells. As Th1 type cytokines, IL-12, IFNγ and the like can be mentioned; as Th2 type cytokines, IL-4, IL-5 and the like can be mentioned.

Considering immunity, particularly tumor immunity, it has been reported that CD8-positive cytotoxic T cells (CTL) and CD4-positive helper T cells play a very important role (North R J. 1984, Greenberg P D. 1991, Pardoll D M. 1998). In particular, it has been reported that CD8-positive T cells (CTL) of immunized animals directly injured target cells in vitro (Wanger H. 1980), and that tumor resistance was conferred to non-immunized animals by adoptive immunity (North R J. 1984, Greenberg P D. 1991). Therefore, how efficiently tumor-specific CTL can be induced is important in the development of antitumor therapy. In antitumor immunity with CTL, CTL recognizes a complex of a major histocompatibility complex (MHC) class I molecule and a tumor antigen-derived peptide, expressed on the tumor cell surface, via a T cell receptor and introduces perforin and the like into tumor cells, thereby exhibiting its cytotoxicity. In the induction of tumor-specific CTL, a focus is placed on first identifying a target antigen peptide that can be specifically expressed in tumor cells, processed in cells, and presented to MHC as a peptide fragment; many peptide molecules that produce high titers of IgG antibodies have been found by the serological analysis of recombinant cDNA expression library (SEREX) method.

However, it is difficult to describe tumor immunity solely based on the identification of a tumor peptide. Many challenges remain unresolved, including how efficiently to present the identified peptide on the cell surface in vivo, and the expression of CD80/CD86, which are co-stimulatory molecules. Speaking in detail, it has been reported that when the peptide is efficiently expressed, but the expression of CD80/CD86 and the like which are co-stimulatory molecules, is low, and the antigen signal alone is transmitted, growth of antigen-specific T cells does not occur and, what is more, T cell anergy develops in the cells that express the antigen (Gribben J G. 1996). In leukemia cells, many gene abnormalities have been shown to be involved in the mechanism for acquiring the growth dominance; it is considered that a specific abnormal protein formed due to such a gene abnormality is expressed, processed and fragmented, and the resulting peptide is presented to the groove of MHC on the cell surface. However, it has been reported to be difficult to induce an effective immune reaction to leukemia (Hirano N. 1996) because the expression of co-stimulatory molecules such as CD80/CD86 on the surface of many leukemia cells is insufficient despite the expression of such a leukemia-specific antigen thereby.

Also, as a recent finding, it has been reported that the reason why tumor rejection does not occur despite an increase of CTL is that the infiltration of immune cells and inflammatory cells is prevented by stroma cells present in the vicinity of the tumor (more than 90% of the tumor tissues of breast cancer, pancreatic cancer, and stomach cancer comprise interstitial fibroblasts), and that the tumor cell regression effect was dramatically increased by removing these disturbances (Yu P. 2004); the infiltration of inflammatory cells and immune cells in tumor cells has been considered to be an important factor concerning tumor regression.

Hence, successful utilization of tumor immunity relies on how efficiently tumor-specific CTL can be induced, and the following problems arise:

Whether or not any tumor-specific antigen has been identified?

What is to do if no tumor-specific antigen has not been identified?

How efficiently is an antigen presented to immunity-inducing cells (dendritic cells and the like)?

How efficiently is the maturation of immunity-inducing cells (dendritic cells and the like) achieved?

How to induce tumor immunity (mainly by CTL) with these points in mind

Efficient infiltration of immune cells in a tumor tissue

Of the above-described problems, whether or not tumor immunity (mainly by CTL) is induced represents the most important requirement; an adjuvant that induces immunity is required for the induction of CTL. As an adjuvant capable of shifting the immune state to Th1-dominant, a patent application for "an adjuvant composed of HVJ-charged liposome" has been published (JP2001-302541A). Some reports are available on the effects thereof as a tumor vaccine [Anticancer Res., (19): 5367-5374. 1999, Ihshda H et al.; Hum. Gene. Ther., (10): 2719-2724. 1999, Zhou W Z. et al.; Gene. Ther., (6): 1768-1773. 1999. Zhou W Z. et al.; Mol. Ther., 5(3), 291-299, 2002. Tanaka M. et al.]. However, concerning the hemagglutinating virus of Japan envelope not in the form of liposome (hereinafter also referred to as HVJ-E), no such effects have been reported to date.

HVJ-E is a vector constructed on the basis of HVJ (JP2002-65278A); it permits the inclusion of a plasmid, oligo-DNA/RNA, protein, peptide, or low molecular compound in a vector vehicle, permits the introduction of the included sample into cells in the vicinity of the vector vehicle in vitro and in vivo, and enables the fusion of cells with each other by the action of the F protein, which is an envelope protein. The present inventors investigated tumor immunity using HVJ-E by making use of the above-described advantages.

Although immune gene therapy is the most suitable method of gene therapy for the metastasis suppression or recurrence prevention of cancer, its effect remains unsatisfactory worldwide. As a cause for this, it is postulated that tumor immunity cannot be enhanced to an extent sufficient to achieve successful treatment. To this end, we have been developing a gene transfer vector and a method of gene expression. As a result, it has become possible to administer an inactivated HVJ envelope as the adjuvant and an anticancer drug, that is encapsulated in the vector, or used in combination therewith, directly into a solid tumor, with coadministration of another anticancer drug, thereby inducing tumor-specific antitumor immunity. In this case, no tumor-specific antigen peptide is required; in other words, this is applicable to a broad range of tumors for which no tumor peptides have been identified. Furthermore, the present invention is groundbreaking in that the situation wherein CTL cells cannot reach the tumor site due to stroma cells and the like surrounding solid tumor tissue, despite induction of CTLs, and hence cannot kill the tumor cells of the solid tumor, so that no tumor regression is observed, can be overcome by using HVJ-E and an anticancer drug in combination.

DISCLOSURE OF THE INVENTION

The present inventors diligently investigated to solve the above-described problems and succeeded in developing a pharmaceutical composition comprising a viral envelope vector in combination with, or encapsulating, a chemotherapeutic agent, as an active ingredient.

Furthermore, as a method more likely to find a clinical application, the inventors introduced an anticancer drug encapsulated in, or used in combination with, a viral envelope vector, directly into a tumor, with coadministration of another anticancer drug, thereby succeeding in inducing tumor cell-specific antitumor immunity also due to the adjuvant action of HVJ-E to regress the tumor.

Therefore, specifically, the present invention provides a pharmaceutical composition wherein an anticancer drug or the like is encapsulated in, or used in combination with, for example, an inactivated HVJ-E vector or the like having the capability of encapsulating a foreign gene.

The present invention further provides a method comprising introducing an HVJ-E vector and the like containing an anticancer drug into a tumor, in combination with administration of another anticancer drug, thereby inducing high antitumor immunity also attributable to the adjuvant effect of the vector to regress the tumor.

The present invention also provides a pharmaceutical composition for treating a solid cancer, particularly urological cancer, which comprises the hemagglutinating virus of Japan envelope and an anticancer drug not encapsulated in the envelope.

There are four points of the gist of the present invention.

First, HVJ is used. Tumor immunity is induced by the adjuvant effect of HVJ.

The second gist resides in that efficient tumor immunity was successfully induced by introducing bleomycin (bleomycin hydrochloride, Bleo for Injection: Nippon Kayaku Co., Ltd.), previously encapsulated in an HVJ-E vector, into transplanted tumor tissue, in combination with systemically administered cisplatin (CDDP, Randa Injection: Nippon Kayaku Co., Ltd.).

Regarding the third gist, the induced CTL cells can be highly efficiently accumulated in the solid tumor.

The third gist also resides in that the induced tumor immunity also retains essential immune actions, including eradication of homologous tumor cells, and that feasibility for use as what is called a neoadjuvant was demonstrated, including the elimination of metastatic tumor by the actions, the prevention of metastasis after surgical operation for surgical elimination of a solid tumor by conducting the treatment in advance, and the killing of metastatic tumors in lymph nodes in the vicinity of the primary tumor to minimize the area to be resected by surgical treatment.

Regarding the fourth gist, a significant antitumor effect was obtained by using HVJ-E and an anticancer drug not encapsulated in HVJ-E in combination.

Accordingly, the present invention provides the following:

(1) An immune adjuvant comprising a viral envelope.
(2) The adjuvant described in (1) wherein the aforementioned adjuvant is an adjuvant for enhancing an immune response.
(3) The adjuvant described in (1) or (2) wherein the aforementioned adjuvant is an adjuvant for enhancing an antitumor immunity.
(4) The adjuvant described in (1) to (3) wherein the aforementioned virus is a virus belonging to a family selected from the group consisting of Retroviridae, Togaviridae, Coronaviridae, Flaviviridae, Paramyxoviridae, Orthomyxoviridae, Bunyaviridae, Rhabdoviridae, Poxviridae, Herpesviridae, Baculoviridae, and Hepadnaviridae.
(5) The adjuvant described in (1) to (4) wherein the aforementioned virus is a species selected from hemagglutinating virus of Japan, retrovirus, adenovirus, adeno-associated virus, herpes virus, vaccinia virus, pox virus and influenza virus.
(6) The adjuvant described in (1) to (5) wherein the aforementioned virus is hemagglutinating virus of Japan.
(7) A viral envelope for use as an immune adjuvant.
(8) A hemagglutinating virus of Japan envelope for use as an immune adjuvant.
(9) A hemagglutinating virus of Japan envelope for use as an antitumor immunity adjuvant.
(10) A use of a viral envelope and cisplatin for improving the tumor antigen-presenting capability of antigen-presenting cell, which results in the accumulation of cytotoxic T-lymphocyte (CTL) cells in a tumor tissue.
(11) A use of a viral envelope, cisplatin and a chemotherapeutic agent for improving the tumor antigen-presenting capability of antigen-presenting cell, which results in the accumulation of cytotoxic T-lymphocyte cells in a tumor tissue.
(12) The use described in (10) or (11) wherein the aforementioned viral envelope is a hemagglutinating virus of Japan envelope (HVJ-E).
(13) The use described in (10) to (12) wherein the aforementioned chemotherapeutic agent is bleomycin.
(14) A method of improving the tumor antigen-presenting capability of antigen-presenting cell, which results in the accumulation of cytotoxic T-lymphocyte cells in a tumor tissue, which method uses a viral envelope and cisplatin.
(15) A pharmaceutical composition for improving the tumor antigen-presenting capability of antigen-presenting cell, which results in the accumulation of cytotoxic T-lymphocyte cells in a tumor tissue, which composition comprises a viral envelope and cisplatin.
(16) A use of a viral envelope and cisplatin for the manufacture of a pharmaceutical for improving the tumor antigen-presenting capability of antigen-presenting cell, which results in the accumulation of cytotoxic T-lymphocyte cells in a tumor tissue.
(17) A pharmaceutical composition comprising a chemotherapeutic encapsulated in a viral envelope vector having an adjuvanticity as an active ingredient.
(18) The pharmaceutical composition described in (17) wherein the chemotherapeutic is an anticancer drug.
(19) The pharmaceutical composition described in (17) or (18) wherein the chemotherapeutic is one or more kinds selected from bleomycins, anthraquinone series carcinostatics, mitomycins, actinomycins, camptothecines, cisplatins, streptozotocin, 5-fluorouracil (5-FU) and derivatives thereof, pirarubicin, and pharmacologically acceptable salts thereof.
(20) The pharmaceutical composition described in (17) to (19) wherein the bleomycins are bleomycin and pharmacologically acceptable salts thereof, and peplomycin and pharmacologically acceptable salts thereof.
(21) The pharmaceutical composition described in (17) to (20) wherein the bleomycins are bleomycin hydrochloride, bleomycin sulfate and peplomycin sulfate.
(22) The pharmaceutical composition described in (17) to (21) wherein the virus having an adjuvanticity is derived from a virus belonging to a family selected from the group consisting of Retroviridae, Togaviridae, Coronaviridae, Flaviviridae, Paramyxoviridae, Orthomyxoviridae, Bunyaviridae, Rhabdoviridae, Poxviridae, Herpesviridae, Baculoviridae, and Hepadnaviridae.
(23) The pharmaceutical composition described in (17) to (22) wherein the aforementioned virus is one kind selected from hemagglutinating virus of Japan, retrovirus, adenovirus, adeno-associated virus, herpes virus, vaccinia virus, pox virus and influenza virus.
(24) The pharmaceutical composition described in (17) to (23) wherein the chemotherapeutic is one or more kinds selected from bleomycin hydrochloride, bleomycin sulfate and peplomycin sulfate, and wherein the virus is hemagglutinating virus of Japan.
(25) The pharmaceutical composition described in (17) to (24), which is an injection.
(26) The pharmaceutical composition described in (17) to (25), which is a therapeutic agent for a solid cancer.
(27) The pharmaceutical composition described in (26) wherein the solid cancer is one kind selected from lung cancer, breast cancer, digestive cancer, head and neck cancer, gynecologic cancer, urological cancer, osteochondrosarcoma, malignant lymphoma and cancer unknown primary.
(28) The pharmaceutical composition described in (27) wherein the digestive cancer is one kind selected from stomach cancer, colon cancer and esophagus cancer.
(29) The pharmaceutical composition described in (27) wherein the head and neck cancer is one kind selected from maxillary cancer, tongue cancer, lip cancer, pharynx cancer, larynx cancer and mouth cancer.
(30) The pharmaceutical composition described in (27) wherein the gynecologic cancer is one kind selected from uterine cancer, ovarian cancer and uterine cervix cancer.
(31) The pharmaceutical composition described in (27) wherein the urological cancer is one kind selected from prostate cancer, bladder cancer, kidney cancer, renal pelvic and ureteral cancer, testicular tumor, adrenal tumor and penis cancer.

(32) A pharmaceutical composition comprising a viral envelope vector having an adjuvanticity as an active ingredient, which is subjected to use in combination with a chemotherapeutic.

(33) The pharmaceutical composition described in (32) wherein the viral envelope vector having an adjuvanticity and the chemotherapeutic are contained in a preparation.

(34) A pharmaceutical composition for inducing antitumor immunity in a living organism, and treating a solid tumor, which comprises an anticancer drug or immunostimulant encapsulated in a hemagglutinating virus of Japan envelope.

(35) A pharmaceutical composition for inducing antitumor immunity in a living organism, and treating a solid tumor, which comprises an anticancer drug or immunostimulant encapsulated in a hemagglutinating virus of Japan envelope, and an additional anticancer drug.

(36) The pharmaceutical composition described in (34) or (35) wherein the hemagglutinating virus of Japan envelope is not in the form of liposome.

(37) The pharmaceutical composition described in (34) to (36) wherein the anticancer drug is bleomycin or a pharmacologically acceptable salt thereof, or peplomycin or a pharmacologically acceptable salt thereof.

(38) The pharmaceutical composition described in (34) or (35) wherein the immunostimulant is a protein comprising granulocyte-macrophage colony-stimulating factor (GM-CSF).

(39) A pharmaceutical composition for inducing antitumor immunity in a living organism, and treating a solid tumor, which comprises a hemagglutinating virus of Japan envelope as an active ingredient, and which is subjected to use in combination with an anticancer drug or immunostimulant.

(40) A pharmaceutical composition for inducing antitumor immunity in a living organism, and treating a solid tumor, which comprises a hemagglutinating virus of Japan envelope as an active ingredient, and which is subjected to use in combination with an anticancer drug or immunostimulant and an additional anticancer drug.

(41) A method of inducing antitumor immunity in a living organism to treat a solid tumor, which comprises administering a pharmaceutical composition comprising an anticancer drug or immunostimulant encapsulated in a hemagglutinating virus of Japan envelope.

(42) A method of inducing antitumor immunity in a living organism to treat a solid tumor, which comprises administering a pharmaceutical composition comprising an additional anticancer drug in addition to an anticancer drug or immunostimulant encapsulated in hemagglutinating virus of Japan envelope.

(43) The method described in (41) or (42) wherein the hemagglutinating virus of Japan envelope is not in the form of liposome.

(44) The method described in (41) to (43) wherein the anticancer drug is bleomycin or a pharmacologically acceptable salt thereof, or peplomycin or a pharmacologically acceptable salt thereof.

(45) The method described in (41) to (44) wherein the immunostimulant is a protein comprising granulocyte-macrophage colony-stimulating factor (GM-CSF).

(46) A use of an anticancer drug or immunostimulant encapsulated in a hemagglutinating virus of Japan envelope for the manufacture of a pharmaceutical that induces antitumor immunity in a living organism to treat a solid tumor.

(47) A use of an anticancer drug or immunostimulant encapsulated in a hemagglutinating virus of Japan envelope and an additional anticancer drug for the manufacture of a pharmaceutical for inducing antitumor immunity in a living organism to treat a solid tumor.

(48) A use of a hemagglutinating virus of Japan envelope as an adjuvant for the manufacture of a drug composition for inducing antitumor immunity in a living organism to treat a solid tumor.

(49) A use of a hemagglutinating virus of Japan envelope as an adjuvant and a vector encapsulating an anticancer drug or immunostimulant for the manufacture of a pharmaceutical for inducing antitumor immunity in a living organism to treat a solid tumor.

(50) A use of a hemagglutinating virus of Japan envelope as an adjuvant and a vector delivering an anticancer drug or immunostimulant for the manufacture of a pharmaceutical for inducing antitumor immunity in a living organism to treat a solid tumor.

(51) A use of a hemagglutinating virus of Japan envelope and an anticancer drug in combination for inducing tumor immunity in a living organism.

(52) A use of a hemagglutinating virus of Japan envelope for introducing cytotoxic T-lymphocyte into solid tumor tissue to induce an antitumor effect.

(53) A use of a hemagglutinating virus of Japan envelope in preoperative auxiliary therapy (neoadjuvant therapy) to induce antitumor immunity in a living organism.

(54) The use described in (46) to (53) wherein the hemagglutinating virus of Japan envelope is not liposome.

(55) The use described in (46) to (54) wherein the anticancer drug is bleomycin or a pharmacologically acceptable salt thereof, or peplomycin or a pharmacologically acceptable salt thereof.

(56) The use described in (46) to (54) wherein the immunostimulant is a protein comprising granulocyte-macrophage colony-stimulating factor (GM-CSF).

(57) A pharmaceutical composition which comprises a hemagglutinating virus of Japan envelope and an anticancer drug for the treatment of urological cancer.

(58) The pharmaceutical composition described in (57) wherein the urological cancer is one kind selected from prostate cancer, bladder cancer, kidney cancer, renal pelvic and ureteral cancer, testicular tumor, adrenal tumor and penis cancer.

(59) The pharmaceutical composition described in (57) or (58) wherein the anticancer drug is at least one kind selected from adriamycin, daunomycin, aclarubicin, amrubicin, idarubicin, epirubicin, pirarubicin, dacarbazine and mitoxantrone.

(60) A pharmaceutical composition for the treatment of bladder cancer, which comprises a hemagglutinating virus of Japan envelope and adriamycin.

(61) A pharmaceutical composition for intravesical injection for the treatment of bladder cancer, which comprises a hemagglutinating virus of Japan envelope and adriamycin.

(62) A use of a hemagglutinating virus of Japan envelope and adriamycin in combination for the treatment of bladder cancer.

(63) A method for the treatment of urological cancer, which comprises administering a hemagglutinating virus of Japan envelope and an anticancer drug.

(64) The method described in (63) wherein the urological cancer is one kind selected from prostate cancer, bladder cancer, kidney cancer, renal pelvic and ureteral cancer, testicular tumor, adrenal tumor and penis cancer.

(65) The method described in (63) or (64) wherein the anticancer drug is at least one kind selected from adriamycin, daunomycin, aclarubicin, amrubicin, idarubicin, epirubicin, pirarubicin, dacarbazine and mitoxantrone.

(66) A use of a hemagglutinating virus of Japan envelope and an anticancer drug for the manufacture of a pharmaceutical for the treatment of bladder cancer.

(67) The use described in (66) wherein the anticancer drug is at least one kind selected from adriamycin, daunomycin, aclarubicin, amrubicin, idarubicin, epirubicin, pirarubicin, dacarbazine and mitoxantrone.

(68) A pharmaceutical composition for the treatment of urological cancer, which comprises a hemagglutinating virus of Japan envelope as an active ingredient, and which is subjected to use in combination with an anticancer drug.

DETAILED DESCRIPTION OF THE INVENTION

Figure 1:
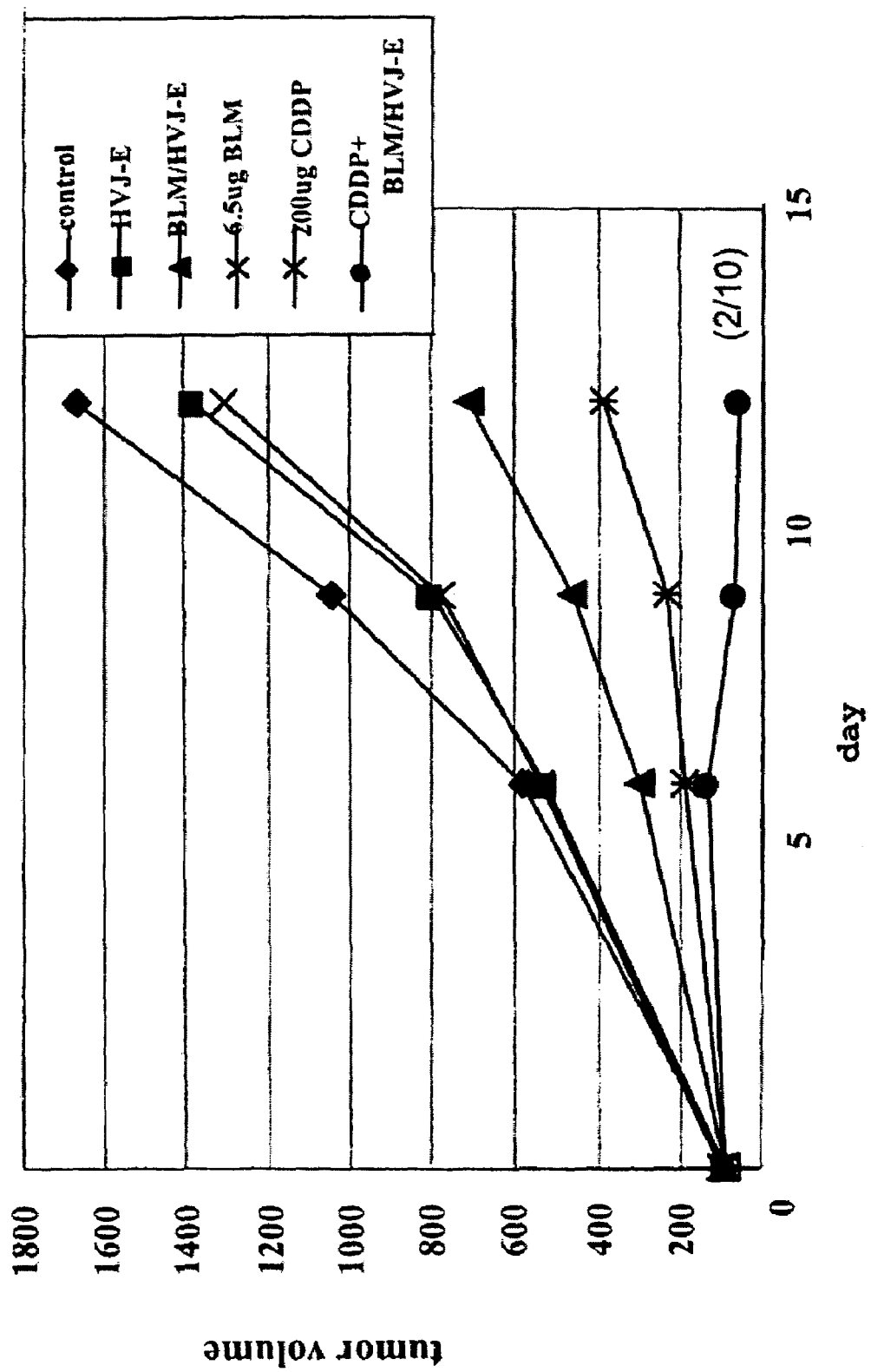
FIG. 1 is a graph comparing the tumor volumes of individual groups.

The present invention is hereinafter described in detail.

The viral envelope in the present invention is a membrane left after removing RNA or DNA from a virus, and is normally utilized for transfection of a gene, polynucleotide, oligonucleotide, plasmid and the like encapsulated therein. Although the viral envelope preferably used in the present invention may be in the form of liposome or not, it is preferably in a form other than liposome.

The kind of the virus is not subject to limitation; specifically, for example, a virus belonging to a family selected from the group consisting of Retroviridae, Togaviridae, Coronaviridae, Flaviviridae, Paramyxoviridae, Orthomyxoviridae, Bunyaviridae, Rhabdoviridae, Poxviridae, Herpesviridae, Baculoviridae, and Hepadnaviridae can be mentioned.

More specifically, as examples of the virus relating to the present invention, hemagglutinating virus of Japan, retrovirus, adenovirus, adeno-associated virus, herpes virus, vaccinia virus, pox virus, influenza virus and the like can be mentioned.

Of these, hemagglutinating virus of Japan (hereinafter also referred to as HVJ), which is one of the mouse pneumonia viruses, can be preferably mentioned.

Specifically, as examples of HVJ, VR-105, VR-907 and the like can be purchased from the American Type Culture Collection (ATCC; address: P.O. Box 1549, Manassas, Va. 20108 USA, TEL[1]-703-365-2700).

http://www.atcc.org/SearchCatalogs/longview.cfm?view=av, 152376, VR-105&text=Sendai&max=20 http://www.atcc.org/SearchCatalogs/longview.cfm?view=av, 1375478, VR-907&text=Sendai&max=20

Viral envelope vectors are described in more detail in, for example, JP2001-286282A (WO 01/57204), JP2002-065278A, WO 03/014338 and the like, and can specifically be prepared in accordance with, for example, Example 8 of JP2001-286282A and the like.

These viral envelopes can be used as immune adjuvants, and are effective in enhancing immune responses and enhancing antitumor effects. Also, when these viral envelopes are used with cisplatin, it is possible to improve the tumor antigen presenting capability of antigen-presenting cells, and thus accumulate cytotoxic T-lymphocyte cells in a tumor tissue.

Major advantages of using a viral envelope are described in detail below.

As stated above, of the viral envelopes, a hemagglutinating virus of Japan envelope (hereinafter also referred to as HVJ-E) is preferably used; HVJ-E causes decreased cytokine induction to dendritic cells, which are antigen-presenting cells, compared with live virus HVJ. In particular, Examples described below have shown that IL-12, which is a Th1 cytokine, is decreased, and that the amount of IL-6 induced is reduced to about ½ compared with HVJ. Even in this case, no increase in Th2 cytokines is observed. Hence, it was found that when using HVJ-E, the amount of cytokines induced decreases but the dendritic cell maturation potential is retained.

In antitumor immunity, although it has been reported that when the ratio of regulatory T cells increases, the subsequent antitumor immunity action is suppressed [Casares N. et al., J Immunol. Dec. 1, 2003; 171(11): 5931-9, Takahashi T. et al., Int Immunol. December 1998;10 (12): 1969-80], HVJ-E acts to lower the ratio of regulatory T cell CD4+CD25+ without influencing the overall ratio of T cells, as shown in an Example below. Because this action is not influenced by an anticancer drug, the use of HVJ-E is highly useful in antitumor immunity.

Such a viral envelope can also be used for preoperative auxiliary therapy (neoadjuvant therapy) to induce antitumor immunity in a living organism.

Furthermore, in addition to cisplatin, a chemotherapeutic may be used together. As a chemotherapeutic preferably used here, bleomycin and the like can be mentioned.

By the viral envelope of the present invention, a method enabling the convenient and safe delivery of an anticancer drug that produces a significant side-effects to the cancer part is provided. Accordingly, the present invention provides a pharmaceutical composition comprising a chemotherapeutic encapsulated in, or used in combination with, a viral envelope having an adjuvanticity, as an active ingredient.

The chemotherapeutic used in the present invention is not subject to limitation, as long as it is a low-molecular compound that acts directly on cells; for example, in Seikagaku Jiten, 3rd edition, published by Tokyo Kagaku Dojin, it is stated that "currently, the coverage of targets of a therapy using chemical substances of highly selective toxicity, i.e., chemotherapy, has been expanded to cover malignant tumors, as well as microbial infections"; antimicrobial drugs, anticancer drugs and the like are of course included in the scope of the chemotherapeutic used in the present invention.

The chemotherapeutic in the present invention is preferably an anticancer drug or an antimicrobial drug. The term anticancer drug as used herein refers to a concept including what are called carcinostatics and antitumor drugs; the terms anticancer, carcinostatics, and antitumor as used herein are synonymous with each other.

As specific examples of the anticancer drug, bleomycins, anthraquinone (anthracycline) series carcinostatics such as adriamycin (doxorubicin), daunomycin (daunorubicin), aclarubicin, amrubicin, idarubicin, epirubicin, pirarubicin, and mitoxantrone, mitomycins, actinomycins, camptothecines such as irinotecan, cisplatins, streptozotocin, 5-fluorouracil (5-FU) and derivatives thereof, pirarubicin, dacarbazine and pharmacologically acceptable salts thereof can be mentioned.

Of these chemotherapeutics, preference is given to anticancer drugs; more preferably, bleomycins, cisplatins or adriamycin can be mentioned; specifically bleomycin or a pharmacologically acceptable salt thereof, or peplomycin or a pharmacologically acceptable salt thereof can be mentioned; more specifically bleomycin hydrochloride, bleomycin sulfate, and peplomycin sulfate can be mentioned.

Cisplatins in the present invention specifically mean carcinostatic platinum complexes such as cisplatin (CDDP), carboplatin [paraplatin] (CBDCA), and nedaplatin.

As specific examples of the antimicrobial drug, oxophosphoric acid, ormetoprim (OMP), trimethoprim, sulfonamids, phosphomycin, penicillin-series antimicrobial drugs, cephalosporin-series antimicrobial drugs, vancomycin, tetracycline-series antimicrobial drugs, rifampicin, fluoroquinone-series antimicrobial drugs and the like can be mentioned.

When using a pharmaceutical composition of the present invention as an anticancer agent, the kind of cancer for which the pharmaceutical composition is indicated is not subject to limitation; specifically, a solid cancer, blood cell cancer and the like can be mentioned. Of these, a solid cancer is a suitable target.

More specifically, as examples of the solid cancer, lung cancer, breast cancer, digestive cancer, head and neck cancer, gynecologic cancer, urological cancer, osteochondrosarcoma, malignant lymphoma, a cancer unknown primary, skin cancer, skin malignant tumor, glioma, thyroid cancer and the like can be mentioned; still more preferably, as examples of the digestive cancer, stomach cancer, colon cancer, esophagus cancer and the like can be mentioned; as the head and neck cancer, maxillary cancer, tongue cancer, lip cancer, pharynx cancer, larynx cancer, mouth cancer and the like can be mentioned; as the gynecological cancer, uterine cancer, ovarian cancer, uterine cervix cancer and the like can be mentioned; as the urological cancer, prostate cancer, bladder cancer, kidney cancer, renal pelvic and ureteral cancer, testicular tumor, adrenal tumor, penis cancer and the like can be mentioned.

Of these solid cancers, skin cancer, skin malignant tumors, head and neck cancers (maxillary cancer, tongue cancer, lip cancer, pharynx cancer, mouth cancer and the like), lung cancer (particularly primary and metastatic squamous cell carcinoma), esophagus cancer, malignant lymphoma (reticulosarcoma, lymphosarcoma, Hodgkin's disease and the like), uterine cervix cancer, glioma, thyroid cancer, prostate cancer, and bladder cancer can be mentioned as more suitable targets.

An immunostimulant may be further encapsulated in, or used in combination with the viral envelope contained in the above-described pharmaceutical composition. Here, as a preferable immunostimulant, proteins, including granulocyte-macrophage colony-stimulating factor (GM-CSF), and the like can be mentioned.

The pharmaceutical composition of the present invention, which comprises an anticancer drug or immunostimulant, is capable of inducing antitumor immunity in a living organism to treat a solid tumor. As used herein, "treat" refers to an action to treat or suppress a solid tumor, specifically means that the solid tumor is regressed, eradicated and the like by injecting the pharmaceutical composition directly into an affected portion or systemically administering the same.

In the step for encapsulating a chemotherapeutic or immunostimulant in a viral envelope, it is preferable to use a surfactant; as specific examples of the surfactant, Triton X100, deoxycholic acid or a salt thereof, cholic acid or a salt thereof, dodecylmaltoside and the like can be mentioned. As the salt of deoxycholic acid, sodium deoxycholate is preferable; as the salt of cholic acid, sodium cholate is preferable.

Specifically, in the case of an inactivated hemagglutinating virus of Japan envelope (HVJ-E) in which an anticancer drug or immunostimulant is to be encapsulated, the anticancer drug or immunostimulant is dissolved in buffer solution. The buffer solution used here is not subject to limitation; specifically, for example, TE buffer solution (10 mM Tris, 1 mM EDTA [pH 8.0]), PBS (phosphate buffer solution) and the like can be chosen and used as appropriate, with preference given to a buffer solution having a pH of 6 to 9.

In addition to the anticancer drug or immunostimulant encapsulated in the viral envelope, the above-described pharmaceutical composition may comprise an additional anticancer drug. As specific examples of the additional anticancer drug, those mentioned to exemplify the aforementioned anticancer drug and the like can be mentioned.

Regarding the method of administration and dosage form of the above-described pharmaceutical composition, any of oral administration and non-oral administration is acceptable; as preparations for oral administration, solid preparations such as powders, granules, capsules, tablets, and chewable tables, and liquid preparations such as solutions and syrups, can be mentioned; as preparations for non-oral administration, injections, ointments, sprays and the like can be mentioned. Preferably, the above-described pharmaceutical composition is given as a preparation for non-oral administration, more preferably an injection.

As the non-human animal, laboratory animals, as well as domestic animals and poultry, are included. The method of administration to a non-human animal may be addition to feed.

The dosage of the above-described pharmaceutical composition varies depending on recipient patient age, body weight, and pathologic condition, method of administration and the like; in a viral envelope composition encapsulating an anticancer drug, it is preferable to administer a titer of normally 15 to 30 mg in the case of, for example, bleomycin, or administer normally about 10 to 100 mg/m$^2$ in the case of cisplatin, based on daily dosage per adult. In a viral envelope composition including an immunostimulant, it is preferable to administer normally about 1,000,000 to 20,000,000 units in the case of, for example, GM-CSF.

Also, based on HVJ-E, normally 40 to 400,000 HAU, preferably 1,200 to 120,000 HAU, and more preferably 4,000 to 40,000 HAU is administered.

In the case of a pharmaceutical composition comprising a viral envelope encapsulating, or used in combination with, an anticancer drug, and an additional anticancer drug, the HVJ-E encapsulating, or used in combination with, the anticancer drug, and the additional anticancer drug, may be prepared separately or together, or may be prepared as a preparation comprising all of them. If they are administered as separate preparations, the routes of administration and dosage forms thereof may be the same or different, and the timings of administration thereof may be the same or different. These are determined as appropriate according to the kinds and effects of the anticancer drugs used in combination.

"In combination" as used herein is understood to mean that the timings of administration thereof may be the same or different, and are not subject to limitation.

The above-described pharmaceutical composition can be prepared as solid preparations such as powders, granules, capsules, tablets, and chewable tables, liquid preparations such as solutions and syrups, injections, sprays, ointments and the like by ordinary methods.

As required in pharmaceutical making, an appropriate pharmaceutically acceptable carrier, for example, an excipient, a binder, a lubricant, a solvent, a disintegrant, a solubilizer, a suspending agent, an emulsifier, an isotonizing agent, a stabilizer, a soothing agent, an antiseptic, an antioxidant, a corrective, a coloring agent and the like are formulated.

As the excipient, organic excipients such as saccharides such as lactose, glucose, and D-mannitol, starches, and celluloses such as crystalline cellulose, inorganic excipients such as calcium carbonate and kaolin and the like can be mentioned; as the binder, gelatinized starch, gelatin, gum arabic, methylcellulose, carboxymethylcellulose, carboxymethylcellulose sodium, crystalline cellulose, D-mannitol, trehalose, hydroxypropylcellulose, hydroxypropylmethylcellulose, polyvinylpyrrolidone, polyvinyl alcohol and the like can be mentioned; as the lubricant, stearic acid, fatty acid salts such as stearates, talc, silicates and the like can be mentioned; as the solvent, purified water, physiological saline and the like can be mentioned; as the disintegrant, low-substitution hydroxypropylcellulose, chemically modified cellulose and starches and the like can be mentioned; as the solubilizer, polyethylene glycol, propylene glycol, trehalose, benzyl benzoate, ethanol, sodium carbonate, sodium citrate, sodium salicylate, sodium acetate and the like can be mentioned; as the suspending agent or emulsifier, sodium lauryl sulfate, gum arabic, gelatin, lecithin, monostearic glycerol, polyvinyl alcohol, polyvinylpyrrolidone, celluloses such as carboxymethylcellulose sodium, polysorbates, polyoxyethylene hardened castor oil and the like can be mentioned; as the isotonizing agent, sodium chloride, potassium chloride, saccharides, glycerin, urea and the like can be mentioned; as the stabilizer, polyethylene glycol, sodium dextran sulfate, other amino acids and the like can be mentioned; as the soothing agent, glucose, calcium gluconate, procaine hydrochloride and the like can be mentioned; as the antiseptic, paraoxybenzoates, chlorobutanol, benzyl alcohol, phenethyl alcohol, dehydroacetic acid, sorbic acid and the like can be mentioned; as the antioxidant, sulfites, ascorbic acid and the like can be mentioned; as the corrective, sweeteners, flavoring agents and the like in common use in the pharmaceutical area can be mentioned; as the coloring agent, coloring agents in common use in the pharmaceutical area can be mentioned.

Featuring the present invention, it is also possible to encapsulate an anticancer drug that causes a severe side-effect or high toxicity in a viral envelope vector, and deliver the anticancer drug directly to cells, without leakage of the anticancer drug into the culture broth in in vitro experiments.

In in vivo animal experiments, not systemic administration, but topical administration, of an anticancer drug can be performed, which enables efficient delivery of the anticancer drug exclusively to the cancer cells of a solid cancer.

Furthermore, in human treatment, a viral envelope vector encapsulating, or used in combination with, an anticancer drug, not only can be administered alone for chemotherapy, but also can be topically administered to an advanced cancer patient not permitting the administration of the anticancer drug to achieve cancer regression; furthermore, radiotherapy and surgical treatment can be used in combination to obtain a still better anti-cancer effect.

For example, for bladder cancer, topical administration such as intravesical infusion is also possible.

A viral envelope vector encapsulating, or used in combination with, an anticancer drug is transfected into host cells in in vitro experiments. The procedures to follow in this operation may employ, for example, a method such as adding a solution of the viral envelope vector encapsulating, or used in combination with, an anticancer drug, to the medium for cultured cells.

For the transfection, provided that the reaction is performed at 37° C., the reaction time is not less than 30 minutes and up to about 48 hours. An evaluation of the effect is preferably performed by viable cell counting or WST assay (a method of counting viable cells: cell counting kit-8, Dojindo Laboratories).

Regarding recipients in in vivo animal experiments, in the case of mouse, for example, it is preferable to use normal mice that are not immunodeficient mice in the case of transplantation of isogenic cancer cells, or nude mice or SCID mice in the case of xenogeneic transplantation.

It is possible to employ a method such as one comprising intradermally transplanting cancer cells cultured in a Petri dish to mice, administering a viral envelope vector encapsulating, or used in combination with, an anticancer drug, into the grown solid cancer lesion after growth of the transplanted cells, measuring the major diameter and minor diameter of the cancer lesion, and determining the anticancer effect thereof.

The present invention further provides a pharmaceutical composition comprising HVJ-E and an anticancer drug. In this case, the above-described treatment of encapsulating an anticancer drug into a viral envelope need not be performed.

As the anticancer drug contained in such a pharmaceutical composition, bleomycins, anthraquinone (anthracycline) series carcinostatics such as adriamycin (doxorubicin), daunomycin (daunorubicin), aclarubicin, amrubicin, idarubicin, epirubicin, pirarubicin, and mitoxantrone, mitomycins, actinomycins, camptothecines such as irinotecan, cisplatins, streptozotocin, 5-fluorouracil (5-FU) and derivatives thereof, pirarubicin, dacarbazine and the like can be mentioned, with preference given to a bleomycin, a cisplatin or adriamycin.

When a pharmaceutical composition relating to the present invention is used as an anticancer agent, the kind of cancer for which the pharmaceutical composition is indicated is not subject to limitation; specifically, a solid cancer, blood cell cancer and the like can be mentioned. Of these, a solid cancer is a suitable target.

More specifically, suitably treated solid cancers are, for example, melanoma, a digestive cancer such as colon cancer, breast cancer, lung cancer, and urological cancer. More specifically, as the urological cancer, prostate cancer, bladder cancer, kidney cancer, renal pelvic and ureteral cancer, testicular tumor, adrenal tumor or penis cancer and the like can be mentioned.

The above-described pharmaceutical composition comprises HVJ-E and an anticancer drug, each of which may be prepared separately or together, or may be prepared as a preparation comprising all of them. If they are administered as separate preparations, the routes of administration and dosage forms thereof may be the same or different, and the timings of administration thereof may be the same or different. These are determined as appropriate according to the kind and effect of the anticancer drug used in combination.

Regarding the methods of administration and dosage forms of the above-described pharmaceutical composition, the same methods of administration and dosage forms as those for the above-described pharmaceutical composition and the like can be mentioned, with preference given to an injection.

As the non-human animal, laboratory animals, as well as domestic animals and poultry, are included. The method of administration to a non-human animal may be addition to feed.

The dosage of the above-described pharmaceutical composition varies depending on recipient patient age, body weight, and pathologic condition, method of administration and the like; for example, in the case of a pharmaceutical composition comprising adriamycin and HVJ-E, normally 40 to 400,000 HAU of HVJ-E and 1 to 500 mg of adriamycin, preferably 4,000 to 40,000 HAU of HVJ-E and about 30 to 60 mg of adriamycin, are administered, based on daily dosage per adult.

The above-described pharmaceutical composition can be prepared as a dosage form by an ordinary method as described above.

EXAMPLES

Hereinafter, specific examples are given below to demonstrate the excellent effects of a pharmaceutical composition comprising a chemotherapeutic encapsulated in, or used in combination with, a viral envelope vector having adjuvanticity according to the present invention, as an active ingredient, particularly the excellent adjuvant effects of viral envelope glycoprotein and the like of the viral envelope vector, but the present invention is never limited by these examples.

Example 1

(1) Study Design

CT-26 cells derived from mouse colon cancer ($5 \times 10^6$ cells) were intradermally transplanted to the backs of 8-week-old male BALB/cAnNCrj mice to yield cancer-bearing mice. Five days after the transplantation, 0.2 mg/body Platocin Injection (cisplatin, CDDP) was intraperitoneally administered to animals wherein the tumor diameter (major diameter) had reached about 5 mm. Following this administration, HVJ-E containing or not containing an anticancer drug (bleomycin hydrochloride [BLM]: Nippon Kayaku Co., Ltd.) and the like were administered into the tumor in a single dose (on the day after administration of cisplatin) or in multiple doses (3 times: 1, 5, and 8 days after administration of cisplatin). Tumor diameters, survival curves, and immune reactions in the tumor tissue were evaluated.

Furthermore, CT-26 cells or isogenic mouse-derived Meth-A cells were transplanted to cancer-bearing mouse receiving the above-described treatment, and the dynamics of the transplanted cells were examined.

(Study 1) The groups described below were established, and the antitumor effects of treatment for transplanted tumors was evaluated.

For modeling, (1) a control group, (2) an HVJ-E group, (3) a BLM-alone group, (4) an HVJ-E/BLM group, (5) a CDDP-alone group, and (6) a CDDP HVJ-E/BLM single dosing group were established; tumor volumes were measured 21 days after each treatment, and the influence on the antitumor effect was examined.

Group composition, dosages and the like are described in detail below.

| group | Test substance intraperitoneal administration (mg/body)* | Test substance intratumoral administration (μg/tumor)** |
|---|---|---|
| Control group | physiological saline 0 | physiological saline 0 |
| HVJ-E group | physiological saline 0 | HVJ-E 0 |
| 6.5 μg/tumor BLM group | physiological saline 0 | BLM 6.5 |
| 6.5 μg/tumor HVJ-E/BLM group | physiological saline 0 | HVJ-E/BLM 6.5 |
| 0.2 mg/body CDDP group | CDDP 0.2 | physiological saline 0 |
| 0.2 mg/body CDDP-6.5 μg/tumor HVJ-E/BLM group | CDDP 0.2 | HVJ-E/BLM 6.5 |

*As cisplatin (CDDP)
**As bleomycin (BLM)

(Study 2) In an attempt to further enhance the antitumor effect of the (single) treatment by single dosing of CDDP HVJ-E/BLM given in Study 1, HVJ-E/BLM was administered in multiple doses (3 times) (Study 2-1). Furthermore, to estimate the kind of any induced antitumor immunity if tumor regression is caused by the induced immunity in the study, tumor cells [CT26 cells (Study 2-2) and BALB/c mouse sarcoma cells Meth-A cells (Study 2-3)] were rechallenged, and the take of the transplanted cells and the increase or decrease in the tumor volume were examined.

(Study 2-1)
Tumor volumes were examined 21 days after treatment for (1) a control group, (2) a CDDP HVJ-E/BLM single dosing group (single treatment), and (3) a CDDP HVJ-E/BLM 3 dosing group.

| group | intraperitoneal administration (mg/body)* | intratumoral administration (μg/tumor)** |
|---|---|---|
| Control group | physiological saline 0 | physiological saline 0 |
| 0.2 mg/body CDDP-6.5 μg/tumor HVJ-E/BLM dosing group | CDDP 0.2 | HVJ-E/BLM 6.5 |
| 0.2 mg/body CDDP-6.5 μg/tumor HVJ-E/BLM 3 dosing group | CDDP 0.2 | HVJ-E/BLM 6.5 × 3 |

*As cisplatin (CDDP)
**As bleomycin (BLM)

(Study 2-2)
Prior to re-transplantation of cells, the same procedures as the above-described study were performed; 15 days after administration of CDDP, CT-26 cells and Meth-A cells ($5 \times 10^6$ cells) were separately intradermally transplanted to a site adjoining the site of the first transplantation of tumor cells, and rejection of the re-transplanted cells was examined.

| group | Rechallenged cells CT-26 | Rechallenged cells MethA |
|---|---|---|
| Control group 1 (with primary CT26 administration) | ◯ | ◯ |
| Control group 2 (without primary CT26 administration) | | ◯ |
| primary 0.2 mg/body CDDP-6.5 μg/tumor HVJ-E/BLM dosing group | | ◯ |
| primary 0.2 mg/body CDDP-6.5 μg/tumor HVJ-E/BLM 3 dosing group | ◯ | ◯ |

(Study 3) As a supplementary study to the results of Study 2, BLM in an amount equivalent to the amount encapsulated was administered directly into the tumor, and its effect was evaluated.

| group | intraperitoneal administration (mg/body)* | intratumoral administration (μg/tumor)** |
|---|---|---|
| 0.2 mg/body CDDP-6.5 μg/tumor HVJ-E/BLM 3 dosing group | CDDP 0.2 | HVJ-E/BLM 6.5 × 3 |
| 0.2 mg/body CDDP-6.5 μg/tumor BLM alone 3 dosing group | CDDP 0.2 | 6.5 × 3 |

*As cisplatin (CDDP)
**As bleomycin (BLM)

(Study 4) CTL Assay
To determine whether or not the antitumor immunity effect observed in the previous study was due to the induction of CT26 cell-specific antitumor immunity, splenocytes recovered from animals were stimulated with CT26 cells, and a CTL assay using radiolabeled chromium was performed to determine whether or not CT26-specific antitumor immunity had been induced.
In this study, (1) a CT-26 cell non-inoculation group, (2) a CT-26 cell-alone inoculation group, (3) a CT-26 cell inoculation+CDDP administration group, and (4) a CT-26 cell inoculation+CDDP+HVJ-E/BLM 3 dosing group were established and tested.

(Study 5) To evaluate the infiltration of CD-4, CD-8, neutrophils, macrophage and the like in the tumor tissues examined in the study of the antitumor effect of the antitumor immunity, the following test groups were established, and tumor tissues were extirpated 9 days after administration of CDDP and subjected to immunohistological staining.

| group | Test substance intraperitoneal administration (mg/body)* | Test substance intratumoral administration (μg/tumor)** |
|---|---|---|
| Control group | physiological saline 0 | physiological saline 0 |
| HVJ-E group | physiological saline 0 | HVJ-E 0 |
| 6.5 μg/tumor BLM alone dosing group | physiological saline 0 | BLM 6.5 |
| 6.5 μg/tumor HVJ-E/BLM dosing group | physiological saline 0 | HVJ-E/BLM 6.5 |
| 0.2 mg/body CDDP dosing group | CDDP 0.2 | physiological saline 0 |
| 0.2 mg/body CDDP-6.5 μg/tumor HVJ-E/BLM dosing group | CDDP 0.2 | HVJ-E/BLM 6.5 |
| 0.2 mg/body CDDP-6.5 μg/tumor HVJ-E/BLM 3 dosing group | CDDP 0.2 | HVJ-E/BLM 6.5 × 3 |

(2) Experimental Methods 2-1) Cultivation of Tumor Cells
CT-26 cells derived from BALB/c mouse colon cancer were cultured using a DMEM medium containing 10% FBS at 37° C. in the presence of 5% $CO_2$.
Cell culture was performed using a 75-cm² flask. After about 80% confluency was reached, passage culture was performed. After the DMEM (containing 10% FBS) broth was removed, the cells were washed with 10 mL of phosphate-buffered saline (PBS), 1 mL of a PBS containing 0.25% trypsin and 1 mmol/L EDTA-2Na was added, and the cells were detached at 37° C. After 9 mL of DMEM medium was added, the cells were harvested, and the cells were recovered via centrifugation (1000 rpm, 5 minutes). After the supernatant was removed, the cells were diluted with a DMEM medium containing 10% FBS and cultured.
BALB/c mouse Meth-A cells were cultured using a DMEM medium containing 10% FBS at 37° C. in the presence of 5% $CO_2$.

2-2) Preparation of Tumor Cell Suspension
After the culture broth of cells reaching about 80% confluency was removed, the culture flask was washed with PBS. A small amount of a PBS containing 0.25% trypsin and 1 mmol/L EDTA-2Na was added, and the flask was allowed to stand at 37° C. until the cells began detached. The cells were harvested using DMEM medium and centrifuged (1000 rpm, 5 minutes). After the supernatant was removed, the cells were suspended in PBS. After centrifugation was performed again (1000 rpm, 5 minutes) and the supernatant was removed, the cells were prepared to $5 \times 10^7$ cells/mL using PBS.

2-3) Mouse Habituation

During the 16-day period of quarantine and habituation, the animals had free access to solid food and drinking water.

2-4) Inoculation of Tumor Cells

After completion of the quarantine and habituation, animals were shaven with clippers. The tumor cell suspension at 100 μL/site (5×10$^6$ cells/body) was administered intradermally to the backs of 59 mice using a disposable syringe and injection needle (26 G). On the day following the administration, the same administration was performed on 57 animals (non-recipient animals).

2-5) Animal Grouping

Tumor diameters (major diameter, minor diameter) were measured 5 days after transplantation (not measured after grouping). Five days later, animals having a tumor diameter (major diameter) of about 5 mm were grouped by stratified randomization to obtain a nearly uniform distribution of mean tumor diameters (major diameters).

2-6) Administration

For the CDDP administration group, a single-dose intraperitoneal administration (1000 μl) was performed using a disposable injection syringe and injection needle. In the sample intratumoral administration group, a desired sample was administered into the tumor (100 μl) after the day of administration of CDDP.

2-7) Measurement of Tumor Diameters

The day of administration was taken as Day 0 after administration. On Days 3, 6, 9, 12, 15, 18, and 21 after administration, all animals had their tumor diameters measured, and tumor volume (major diameter×minor diameter×minor diameter÷2) was calculated.

Regarding rechallenges of CT-26 cells and Meth-A cells as well, tumor diameters were measured after each rechallenge.

2-8) CTL Assay

The spleen was extirpated from each anesthetized animal and recovered in a Petri dish (6 cm in diameter) containing 3 ml of RPMI solution. The spleen tissue was squashed between the frosted portions of two sterile glass slides, splenocytes were separated from the coat to the maximum possible extent, and the debris was removed through meshes. After 7 ml of PRMI solution was added, the cells were centrifuged at 1200 rpm for 10 minutes, and the supernatant was removed. The cells were washed by the addition of additional 10 ml of RPMI solution. The washing procedure was performed again, and the cells obtained by this procedure were suspended in 5 ml of GIT (containing 10% FCS and antibiotics) solution. The cells obtained from this operation were counted. After adjustment to 5×10$^6$ cells/ml, these cells were sown to a 12-well plate at 2 ml/well. CT-26 cells as stimulating cells were added to the wells. The stimulating cells were prepared by adding 100 μl of mitomycin C to a GIT solution containing the stimulating cells adjusted to 1×10$^7$ cells/ml, and treating at 37° C. for 1 hour. After the treatment, 9 ml of GIT solution was added, the cells were centrifuged at 1000 rpm for 5 minutes, and the supernatant was removed, after which the cells were washed by the addition of 10 ml of GIT solution, the washing procedure was performed again, and finally the cells were suspended in 1 ml of GIT solution to yield a cell suspension. The suspension was adjusted to a cell density of 2.5×10$^5$ cells/ml by the addition of GIT solution, and 2 ml of the solution was added to a suspension of the cells recovered from the aforementioned spleen tissue.

For the sample without the stimulating cells, 2 ml of GIT solution alone was added. The sample was cultured for 6 days. In CTL assay, these cells were used as the target.

CTL assay was performed using a cultured sample of splenocytes recovered from the tissue. First, CT-26 cells for use as target cells were prepared as described below. A solution of CT-26 cells was adjusted to 1×10$^7$ cells/ml (in GIT medium), 150 μl of this solution was taken, 150 μl of a Cr solution, previously radiolabeled at 1 mCi/ml, was added to the solution, and the cells were cultured at 37° C. for 1 hour. After 10 ml of GIT solution was added, the cells were washed and centrifuged at 1000 rpm for 5 minutes, and the cells were recovered. The supernatant was removed, and the cells were washed by the addition of 10 ml of GIT solution. This washing procedure was performed three times in total. The cells obtained by the operation were suspended in 150 μl of GIT solution, the suspension was diluted 100 fold to obtain a final concentration of 1×10$^5$ cells/ml, and this diluted suspension was used as target cells (T) in the procedures described below.

Effector cells (E) were prepared from treated cells recovered from the four groups described in the Method section, and used.

Actual CTL assay was performed with the ratio of effector cells (E) and target cells (T), E/T ratio, set at 80, 35 40, 20, 10, and 5. In this operation, 100 μl of target cells (1×10$^5$ cells/ml) were added to make a total quantity of 200 μl. The sample was treated at 37° C. for 4 hours.

After completion of the cultivation, the cells and the debris were removed via centrifugation, 100 μl of the supernatant was recovered and placed in a γ-counter, and radioactivity was counted. % specific Cr release was calculated using the equation below.

% specific $Cr$ release=$b-c/(a-c)*100$(%)

a: maximum release (cpm)
b: experimental release (cpm)
c: spontaneous release (cpm)

2-9) The tumor tissue was frozen in liquid nitrogen in preparation for staining the tumor tissue. The tumor tissue was cut into sections 8 μm in thickness using a cryostat. The tissue sections were fixed in −20° C. cold acetone for 15 minutes. After the sections were washed with water, endogenous avidin-biotin blocking was performed, and the sections were washed with water. The sample was reacted with normal rabbit serum and 50-fold diluted primary antibody [anti-mouse CD8a rat antibody (Ly-Z; Pharmingen) or anti-mouse CD4a rat antibody (L3T4; Pharmingen)] at 4° C. overnight. After the sample was washed with 7.5 mM Tris buffer solution (pH 7.5), it was reacted with 300-fold diluted anti-rat biotin-labeled rabbit Ig (DAKO) for 30 minutes. After the sample was washed with 9.5 mM Tris buffer solution (pH 7.5), it was reacted with 100-fold diluted streptoavidin for 30 minutes. After the sample was washed with 11.5 mM Tris buffer solution (pH 7.5), a color was developed with Fast Red. After the sample was washed with water, the nuclei were stained with hematoxylin.

Results

Results of Study 1

Tumor volumes for (1) the control group, (2) the HVJ-E group, (3) the BLM-alone group, (4) the HVJ-E/BLM group, (5) the CDDP-alone group, and (6) the CDDP+HVJ-E/BLM single dosing group were measured.

The study was performed on a total of 10 animals for each group in two separate sessions involving five animals each. A noteworthy finding in the study was that the transplanted tumor cells disappeared apparently and remission occurred in 2 of the 10 test animals in (6) the CDDP+HVJ-E/BLM single dosing group. In one of the two tests, the mean values of the tumor volumes of the five animals are plotted on a graph. The mean tumor volumes were 1641 mm³ for (1) the control group, 1386 mm³ for (2) the HVJ-E group, 1303 mm³ for (3) the BLM-alone group, 718 mm³ for (4) the HVJ-E/BLM group, 387 mm³ for (5) the CDDP-alone group, and 51 mm³ for (6) the CDDP HVJ-E/BLM single dosing group. The mean values relative to the mean tumor volume for the control group as 100% were 82.9%, 80.0%, 43.0%, 23.2%, and 3.1% for (2) the HVJ-E group, (3) the BLM-alone group, (4) the HVJ-E/BLM group, (5) the CDDP-alone group, and (6) the CDDP HVJ-E/BLM single dosing group, respectively (FIG. 1).

Results of Study 2-1

Models for (1) the control group, (2) the CDDP+HVJ-E/BLM single dosing group, and (3) the CDDP+HVJ-E/BLM 3 dosing group (HVJ-E/BLM administered at 1, 5, and 8 days after administration of CDDP) were prepared, and effects on tumor rejection were examined in the (2) the CDDP+HVJ-E/BLM single dosing group and (3) the CDDP+HVJ-E/BLM 3 dosing group.

Figure 2:
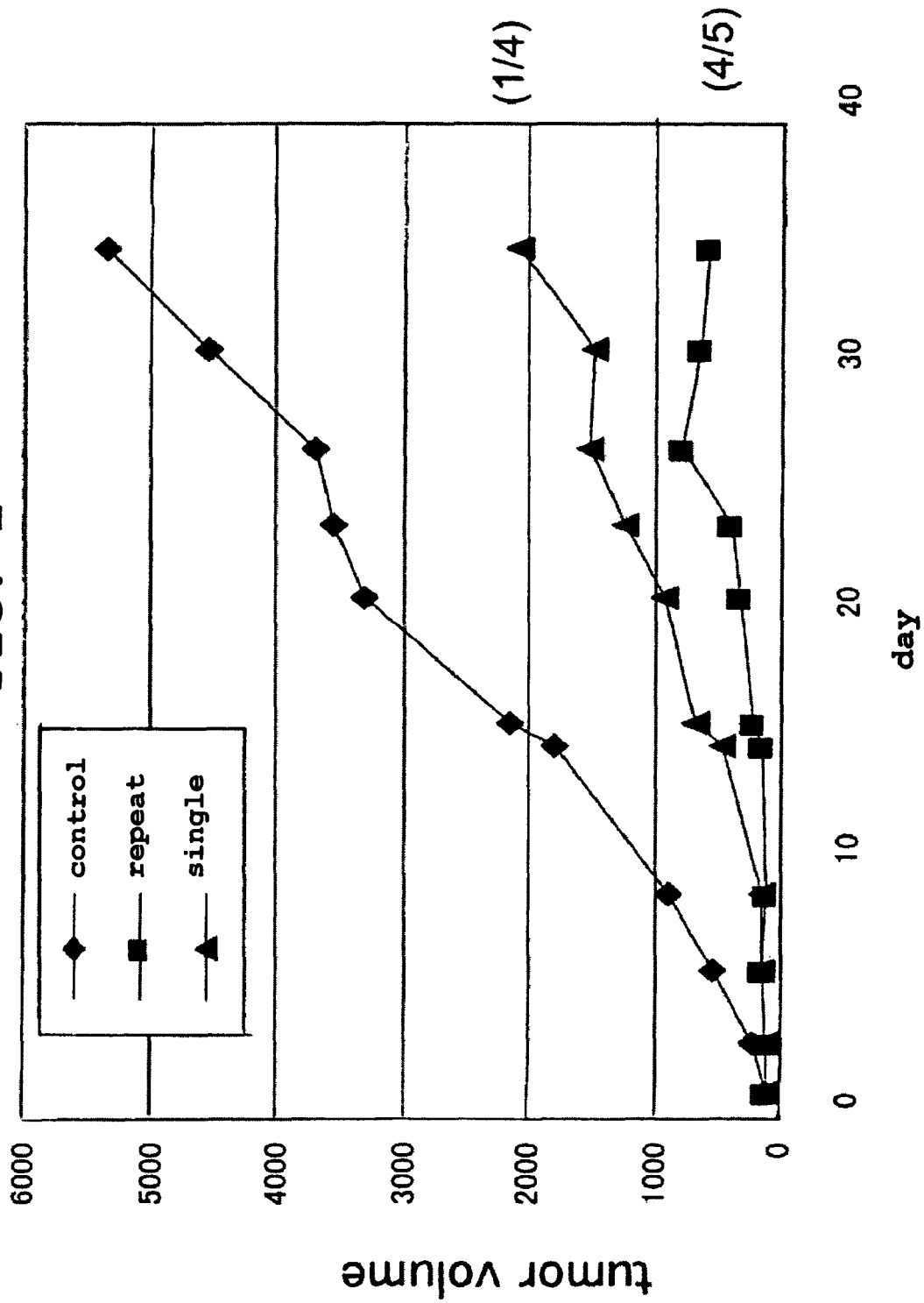
FIG. 2 is a graph comparing the antitumor effects of single and multiple dosing of CDDP and HVJ-E/BLM.

First, as shown in the figure, remission was observed in 1 of the 4 mice in the group (2). Remission was observed in 4 of the 5 mice in the group (3). (FIG. 2)

Results of Studies 2-2 and 2-3

Figure 3:
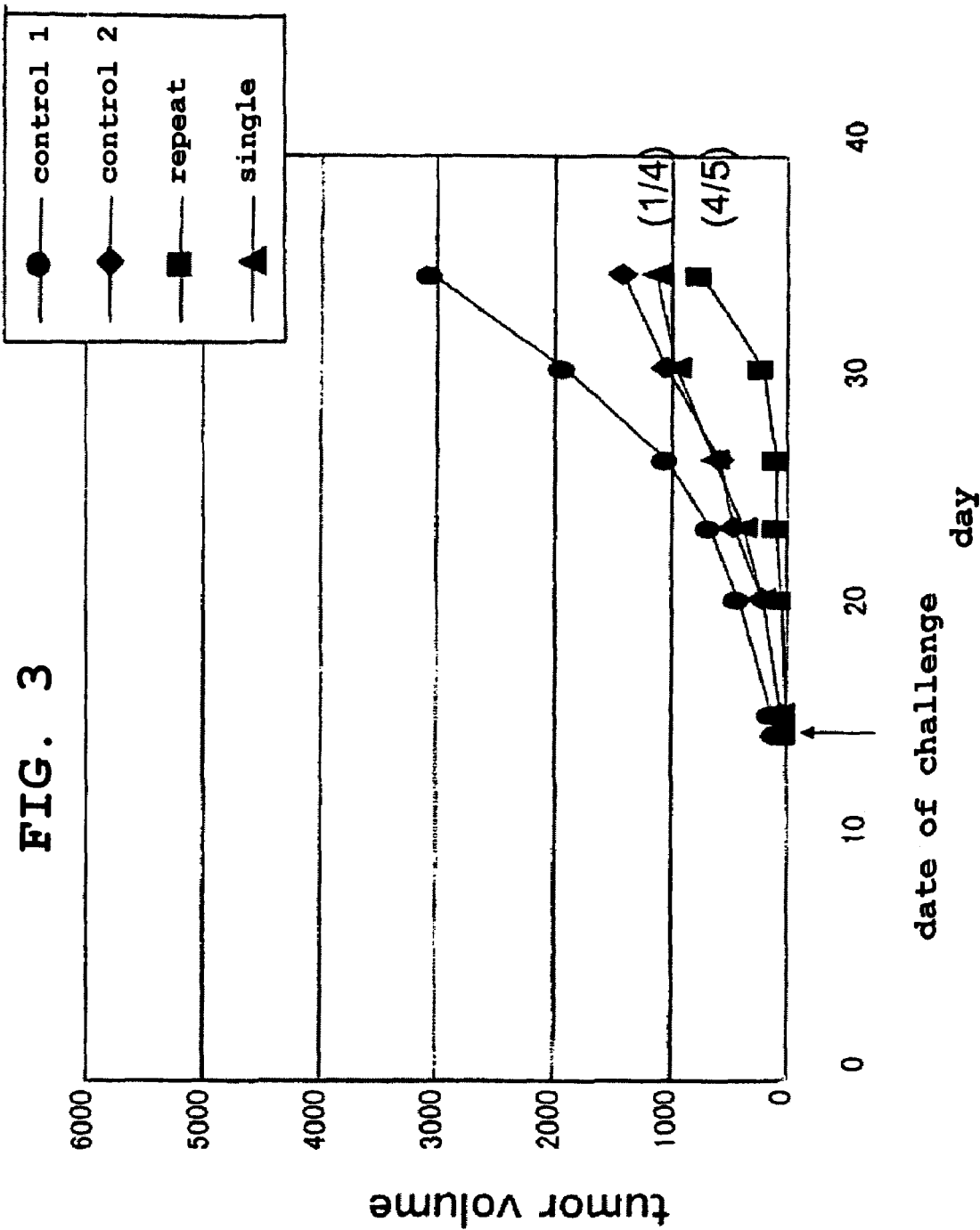
FIG. 3 is a graph comparing tumor immunity-inducing effects in a study of rechallenge of isogenic tumor cells. Rechallenge was performed on Day 15.

In the study of rechallenge of isogenic tumor cells (CT-26 cells) performed in Study 2-2, remission occurred in 1 of the 4 mice in the CDDP+HVJ-E/BLM single dosing group; this mouse received re-inoculation of CT-26 cells and rejected the transplanted cells. However, in the remaining three animals, the primary tumor cells were not rejected; these animals received re-transplantation of CT-26 cells and could not reject the cells after re-transplantation. On the other hand, 4 of the 5 animals in the CDDP+HVJ-E/BLM 3 dosing group exhibited rejection. From the results shown above, it was confirmed that tumor immunity had been induced (FIG. 3). Whether or not the tumor immunity is specific for CT-26 cells was determined by the next study.

Figure 4:
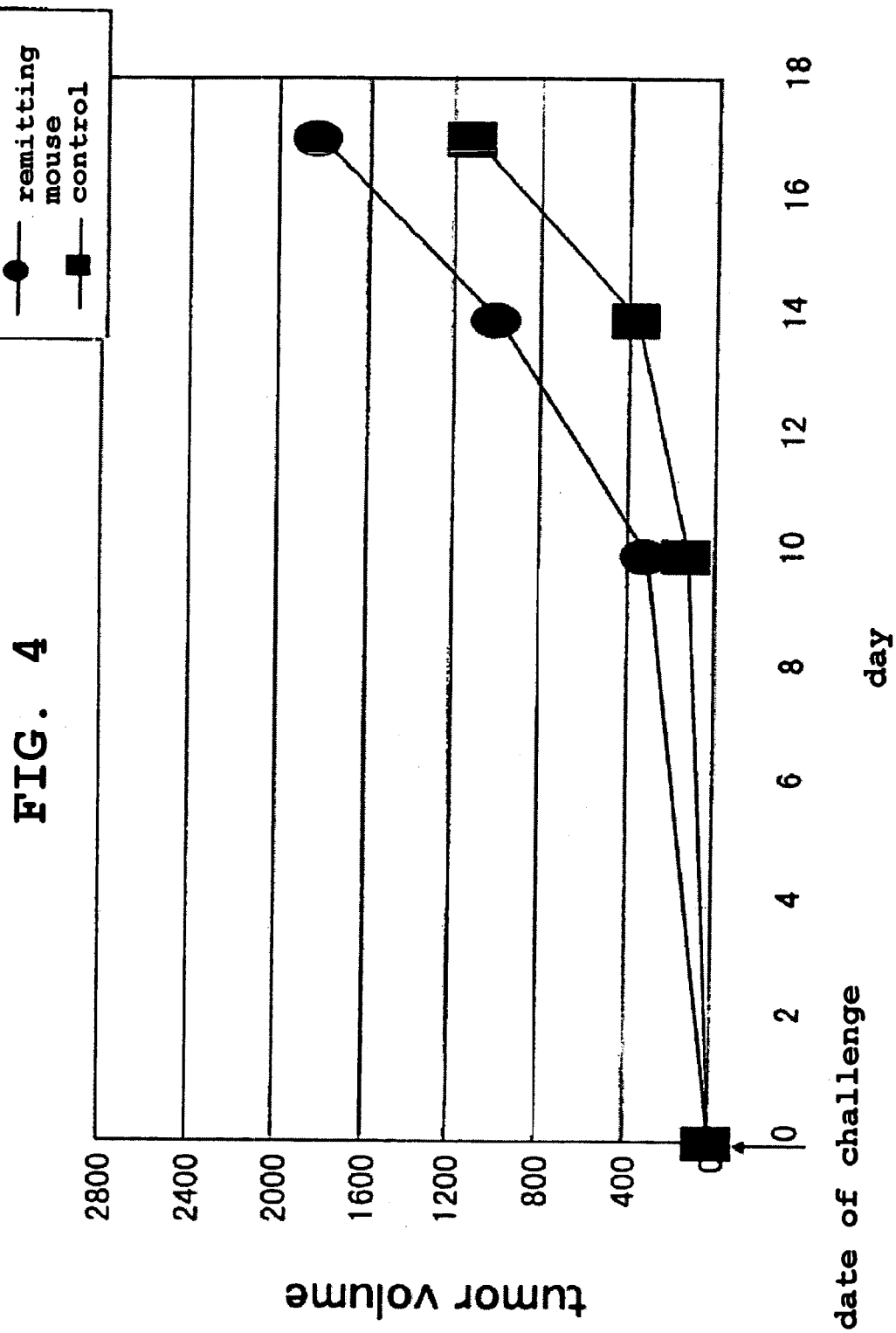
FIG. 4 is a graph comparing tumor immunity-inducing effects in a study of rechallenge of isogenic different tumor cells. Rechallenge was performed on Day 0.

In the tests performed in Study 2-3, Meth-A cells transplanted to mice achieving remission by CDDP+HVJ-E/BLM 3 dosing could not be rejected (FIG. 4).

Results of Study 3

Figure 5:
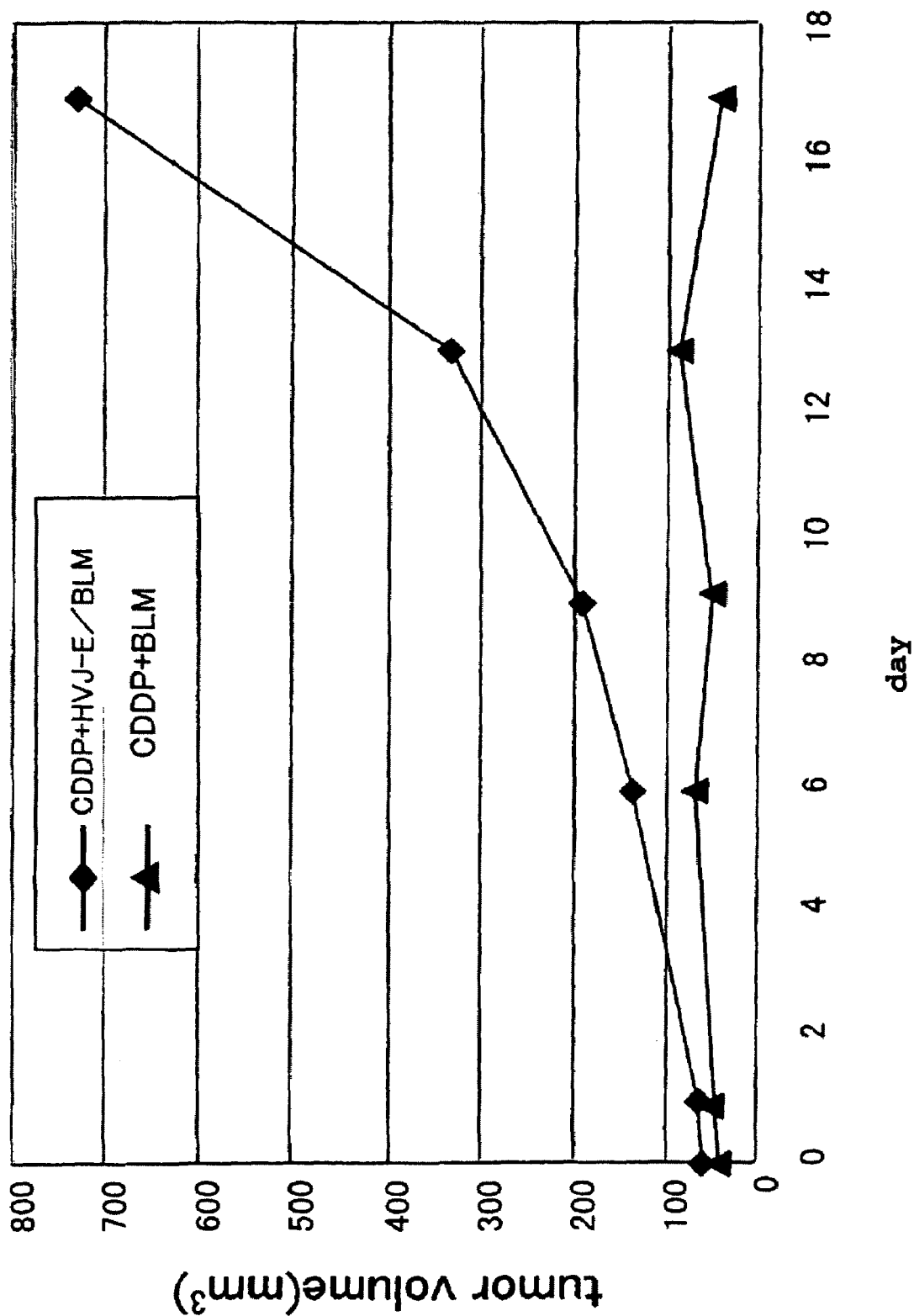
FIG. 5 is a graph showing comparison of the antitumor effects between CDDP and BLM, and CDDP and BLM encapsulated in HVJ-E.

In the studies performed previously, an antitumor effect was observed with CDDP+HVJ-E/BLM. However, regarding the effect of BLM in those studies, the influence of the presence or absence of HVJ-E, i.e., the influence of the encapsulation of BLM in HVJ-E (including the adjuvant effect of HVJ), had not been evaluated; in the present study, the effect with coadministration of CDDP was evaluated. The results are shown in FIG. 5. As is evident from the figure, the tumor regression effect of the treatment was much lower, and the tumor could not be regressed, in the study performed with BLM not encapsulated in HVJ-E, compared with BLM encapsulated in HVJ-E. It was found that even when BLM was introduced directly into tumor tissue with coadministration of CDDP, no tumor regression effect was observed unless BLM was encapsulated in HVJ-E and introduced into the tumor tissue.

Results of Study 4

The results of the experiments performed in Studies 1 and 2 demonstrated the following facts when CDDP was administered systemically and BLM encapsulated in HVJ-E was administered directly into tumor tissue.

Tumor tissue can be regressed.

The effect is enhanced when a sample of BLM encapsulated in HVJ-E is administered more than one time.

Mice achieving remission wherein transplanted cells were regressed by the treatment received re-transplantation of the cells and rejected the re-transplanted cells.

However, when different isogenic cells were transplanted to the mice achieving remission, the transplanted cells could not be rejected.

Thus, it was estimated that immunity specific for the transplanted cells was induced in the study; to examine direct induction of specific immunity, it was examined whether or not immunity specific for CT-26 cells was induced.

Figure 6:
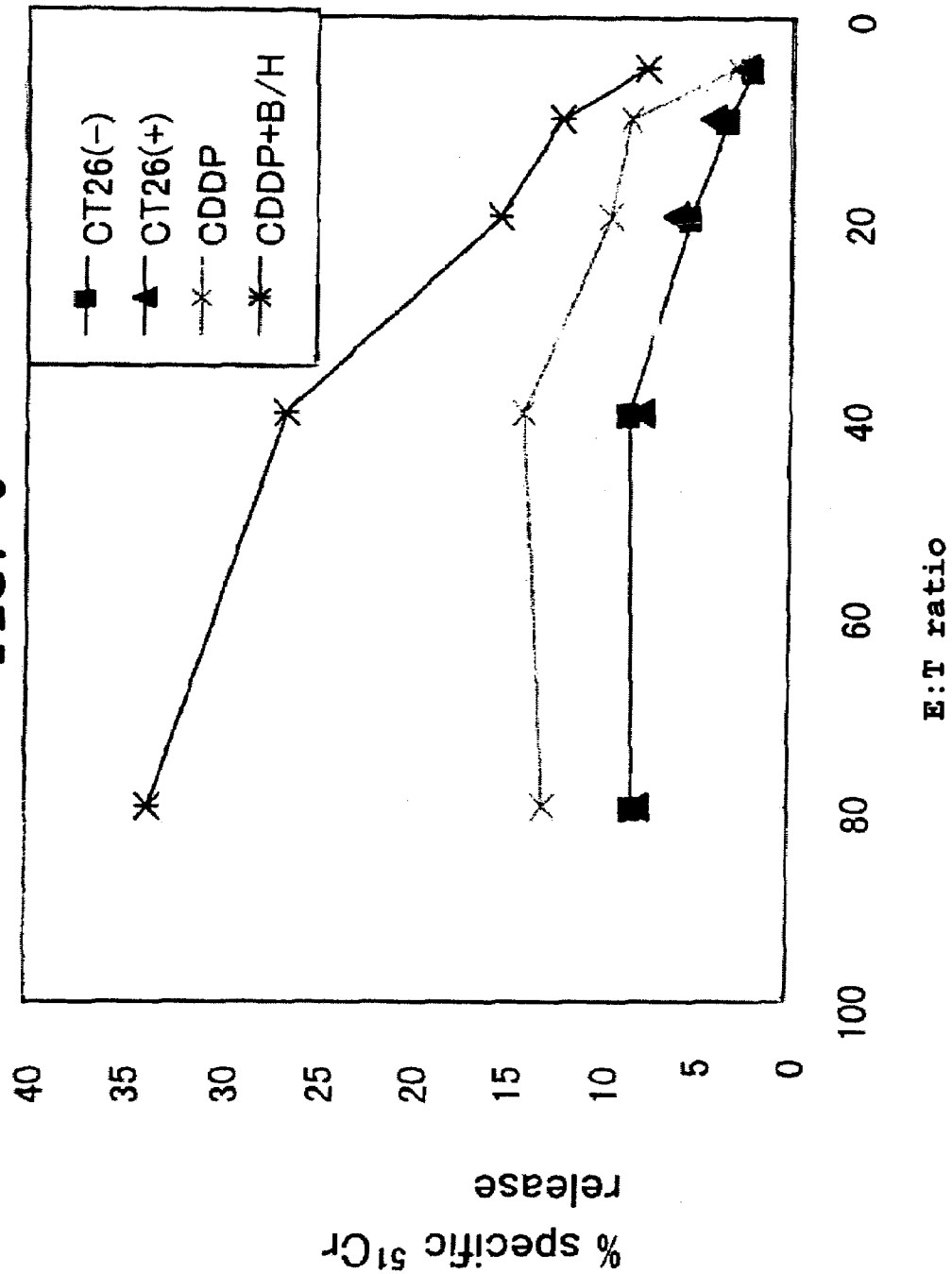
FIG. 6 is a graph showing CTL induction by CTL assay.

(1) A CT-26 cell non-inoculation group, (2) a CT-26 cell-alone inoculation group, (3) a CT-26 cell inoculation+CDDP dosing group, and (4) a CT-26 cell inoculation+CDDP+HVJ-E/BLM 3 dosing group were established, and CTL assay was performed to examine CT-26 cell-specific CTL. The ratio of effector cells (E) and target cells (T), E/T ratio, was varied, and CTL induction was quantified by % specific Cr release. As a result, as seen from FIG. 6, when the ET ratio was 80%, the % specific Cr release was 8.1% for (1) the CT-26 cell non-inoculation group, 8.1% for (2) the CT-26 cell-alone inoculation group, 12.9% for (3) the CT-26 cell inoculation+CDDP dosing group, and 33.5% for (4) the CT-26 cell inoculation+CDDP+HVJ-E/BLM 3 dosing group.

From the results above, it was found that CT-26 cell-specific CTL induction occurred in (4) the CT-26 cell inoculation+CDDP+HVJ-E/BLM 3 dosing group.

Results of Study 5

Figure 9:
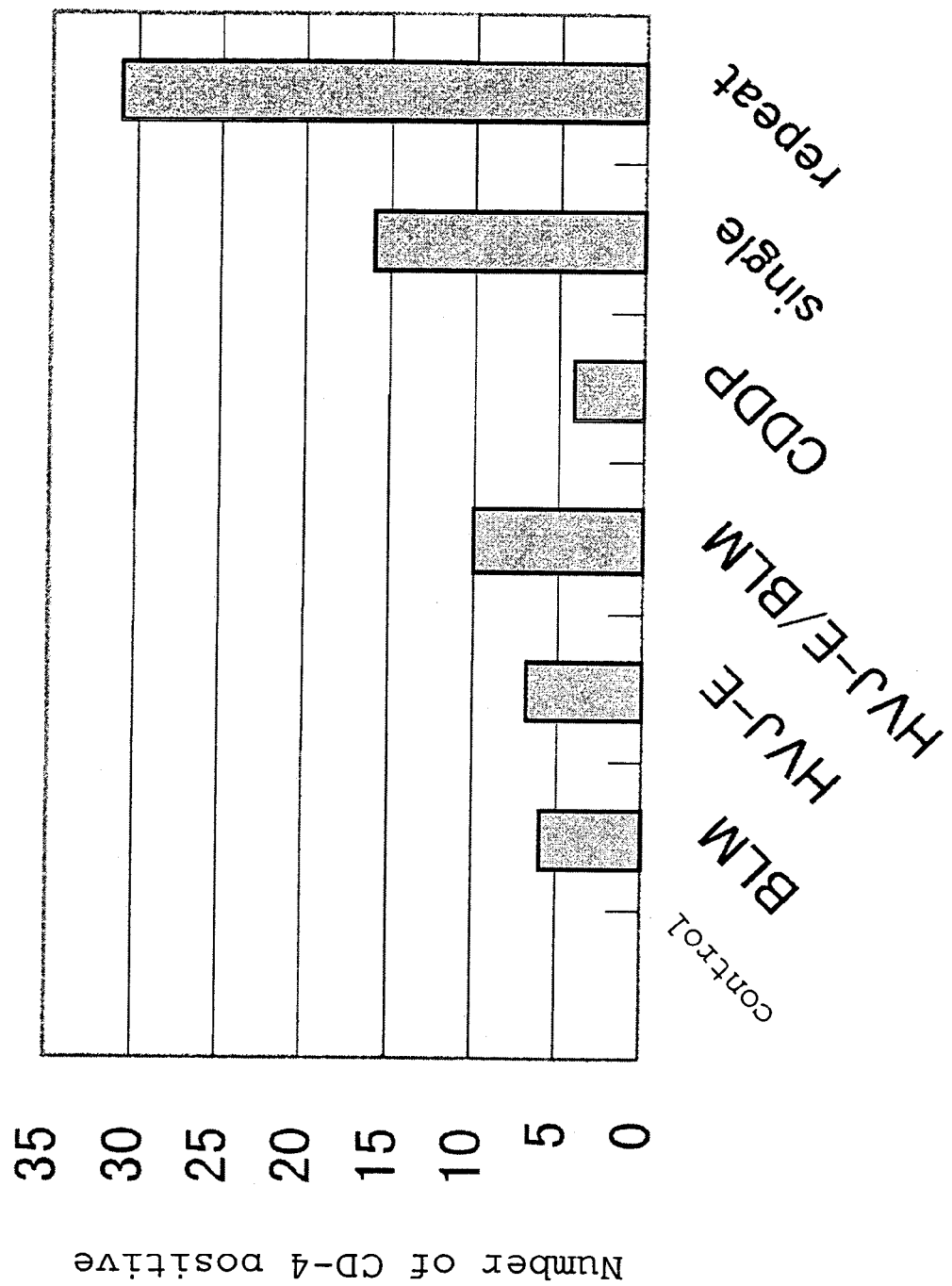
FIG. 9 is a graph comparing the CD-4-positive images for individual groups.
Figure 10:
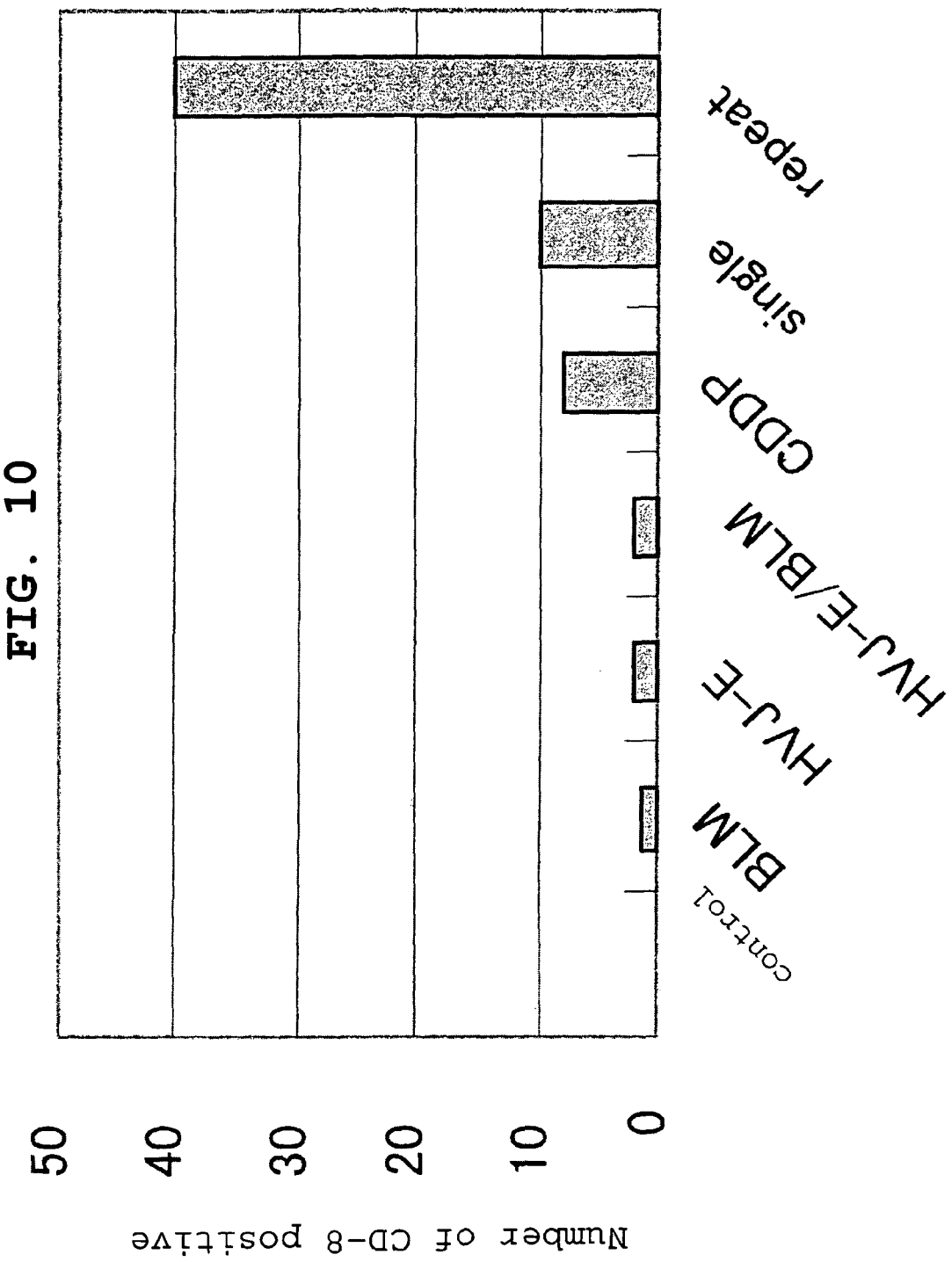
FIG. 10 is a graph comparing CD-8-positive images for individual groups.

(1) A control group, (2) an HVJ-E group, (3) a BLM-alone group, (4) an HVJ-E/BLM group, (5) a CDDP-alone group, (6) a CDDP+HVJ-E/BLM single dosing group, and (7) a CDDP, HVJ-E/BLM 3 dosing-group were established; tumor tissues were collected from the animals at 9 days after CDDP administration, and sections of the tissues were prepared for each group. First, characteristic pathological findings observed in the tissues with HE staining (FIGS. 7 and 8) and anti-CD-4 antibody and anti-CD-8 antibody specific immunohistological staining (data not shown) are described. (1) In the control group, malignant cell findings specific for tumor cells, i.e., nuclear division in many cells and high nuclear density, were observed. At the center of the tumor tissue, necrotic cell death was observed. The majority of the cells had a morphology characteristic of sarcoma cells, i.e., vigorous growth of CT-26 cells was observed. Almost no CD-4 or CD-8 (FIGS. 9 and 10)-positive cells were observed. In (2) the HVJ-E group, the findings were generally the same as (1) the control group; neutrophil infiltration was observed in the vicinity of the needle prick where HVJ-E was injected. Generally similar findings were obtained from (3) the BLM-alone group and (4) the HVJ-E/BLM group.

Compared with these groups, in (5) the CDDP-alone group, tumor cell necrotic signs were observed over a wide range of the tumor tissue. It was considered that the intraperitoneally administered CDDP spread in the tumor tissue via blood vessels and the like and affected the tumor cells by its effect as an anticancer drug. However, with administration of CDDP alone, not all tumor cells were eradicated, with some tumor cells remaining; it was postulated that the tumor growth observed 9 days after CDDP administration was attributable to the remaining cells. In (6) the CDDP HVJ-E/BLM single dosing group, tumor cells decreased generally, and a considerable number of tumor cells disappeared. The day this sample was recovered was Day 9 of administration of CDDP, when a remission state had not been reached; it remains unknown whether or not this sample can achieve remission. It should be noted, however, that the numbers of CD-4- and CD-8-positive cells (FIGS. 9 and 10) increased but were smaller than those obtained with the multiple dosing of HVJ-E/BLM described below. In (3) the CDDP HVJ-E/BLM 3 dosing group, no or almost no tumor cells were observed, antigen fibers showed denaturation and necrosis, with liquefied sites observed. Generally, there were a small number of cells, and neutrophil infiltration was observed over a wide range. Characteristically, anti-CD-4 antibody- and anti-CD-8 antibody-positive cells (FIGS. 9 and 10), which were not conspicuously in other tissues, were observed over a wide range. It has been reported that anti-CD-8 antibody positive cells that infiltrate in a tumor tissue are mostly CTL cells; judging from this finding, combined with the results of Study 4, it was postulated that in (3) the tumor remission observed in the CDDP HVJ-E/BLM 3 dosing group was due to CTL.

In this Example, it was shown that (1) the vaccine effect of dendritic cells increased with the addition of CpG-ODN, and that (2) antitumor immunity was induced by the synergistic effect of intratumoral administration of HVJ-E/BLM and systemic administration of CDDP.

As characteristics of the present invention, the following can be mentioned.

Tumor remission was observed.

As a reason for the remission, an effect of infiltration of CD-8-positive cells in the tumor tissue, i.e., tumor cell-specific CTL, is likely.

Because efficient tumor immunity cannot be induced solely by administration of HVJ-E/BLM or CDDP alone, their combination is important.

When CDDP was administered, its effect was weak but covered the entire tumor tissue, and subsequent administration of HVJ-E/BLM efficiently delivered HVJ-E/BLM to the tumor tissue made brittle by the CDDP, and the HVJ-E/BLM fully exhibited the effect thereof.

In this process, HVJ-E acts as an adjuvant to induce tumor immunity.

Captions for the Immunostaining Images

Figure 7:
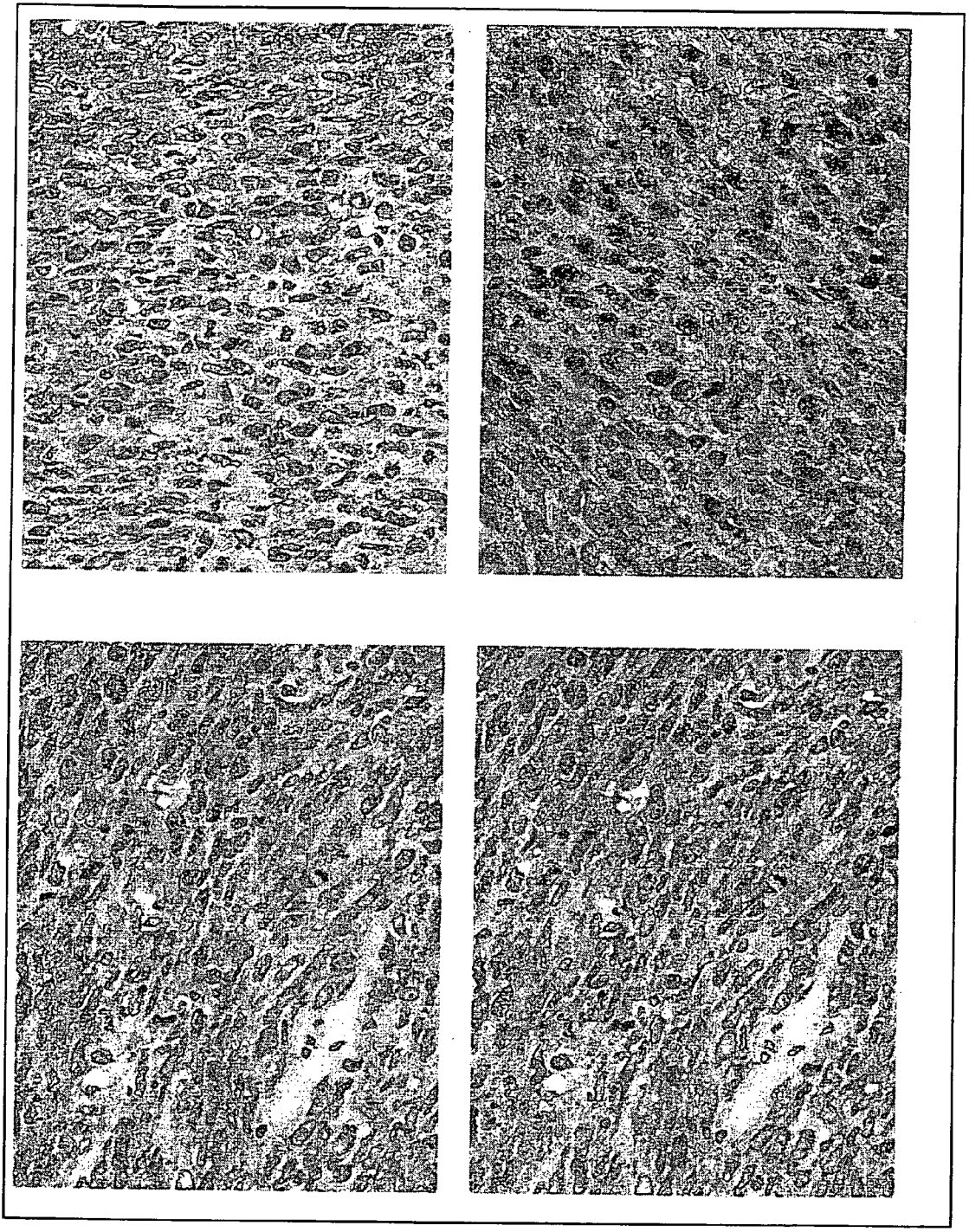
FIG. 7 shows HE staining images of individual tumor tissue sections. These are hematoxylin-eosin (HE) staining images for (1) control group [upper right], (2) HVJ-E group [lower right], (3) BLM-alone group [upper left], and (4) HVJ-E/BLM group [lower left].
Figure 8:
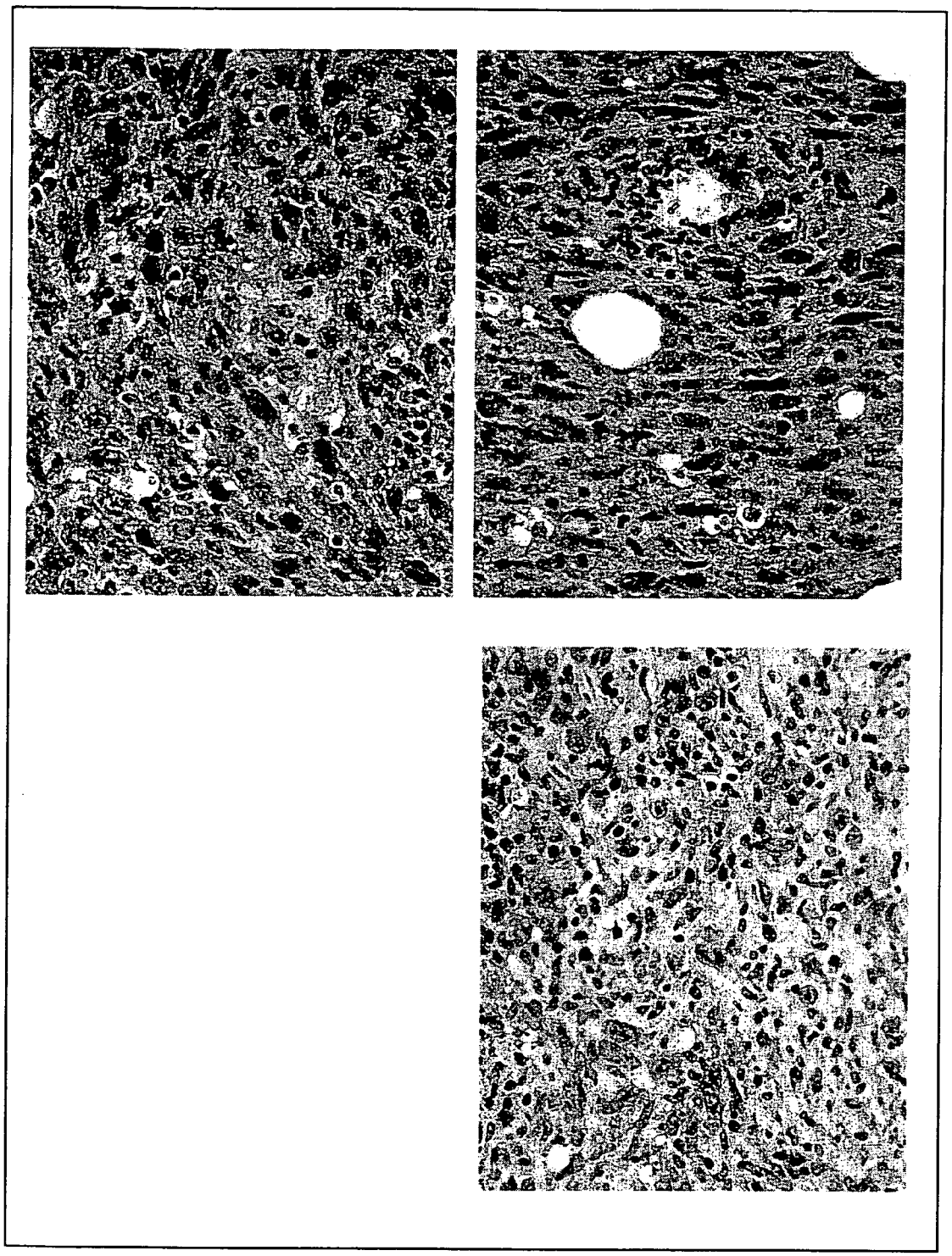
FIG. 8 shows hematoxylin-eosin (HE) staining images for (5) CDDP-alone group [upper right], (6) CDDP+HVJ-E/BLM 25 single dosing group [lower right], and (7) CDDP+HVJ-E/BLM multiple dosing group [upper left].

Captions for the HE Staining Images in FIGS. 7 and 8

In the controls, malignant findings are observed, including high nuclear density, hyper chromatin, lack of nuclear size uniformity, and high frequency of nuclear division, in the CT-26 cancer cells. Similar findings of this phenomenon were observed with the administration of HVJ-E, BLM, and HVJ-E/BLM, though there was some variation. Neutrophil and macrophage infiltration was observed in the necrotized portions. In the CDDP administration samples, vacuolar degeneration is observed, with neutrophils, macrophage and the like infiltrating in the cancer cells; it is seen that these cells surround the cancer cells. With single dosing of CDDP+HVJ-E/BLM, the number of tumor cells decreased, whereas many lymphatic cells are observed. The HE staining density decreased, showing more pinkish images. This provides evidence for a reduction in the nucleic acid concentration in the cells, and is considered to be due to a reduction in the cell density of the cancer cells. With three dosing of CDDP+HVJ-E/BLM, almost no cancer cells were observed, with only a few cells showing cell division, and the cells lost the capability of growing. Many portions showed denaturation or necrosis, inflammatory cell infiltration was observed over a wide range, and many lymphocytic cells were observed.

Example 2

(1) Study Design

B49 Cell-Inoculated Mouse Model

This experimental model can be prepared in accordance with, for example, a method described in *Anticancer Res.*, 2004, 24(4):2225-30, and the like.

Figure 11:
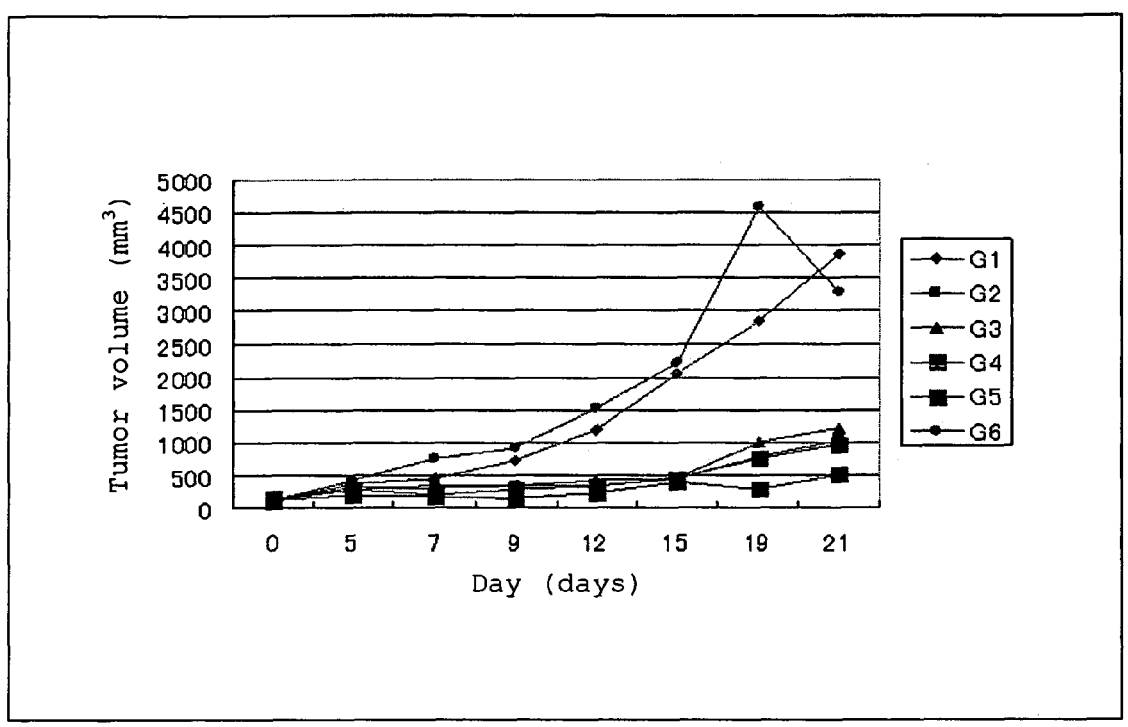
FIG. 11 is a graph comparing changes in tumor volume among different groups of animals in a mouse model inoculated with bladder cancer cells.

Specifically, $2 \times 10^6$ MB49 cells were intradermally inoculated to the backs of B6 mice, and the animals were allowed to stand for 5 days; a sample for each of the groups G1 to G6 was inoculated three times to the tumors of animals having tumor diameters of 7-8 mm, and their effects were evaluated.
G1; physiological saline (control)
G2; adriamycin (ADM) 20 µg
G3; ADM 100 µg
G4; ADM 20 µg+HVJ-E 5000 HAU
G5; ADM 100 µg+HVJ-E 5000 HAU
G6; HVJ-E 5000 HAU (2) Results Changes over time in tumor volume ($mm^3$) for individual groups are shown below. (see FIG. 11)

|  |  | Group | | | | | |
| --- | --- | --- | --- | --- | --- | --- | --- |
|  |  | G1 | G2 | G3 | G4 | G5 | G6 |
| Day | 0 | 120 | 128.4 | 119 | 125.3 | 117.6 | 120.5 |
|  | 5 | 351.1 | 303.2 | 285.8 | 266.6 | 199.1 | 423.6 |
|  | 7 | 442.5 | 330 | 291.2 | 190.6 | 152.6 | 734.1 |
|  | 9 | 717.6 | 324.9 | 333.9 | 267.5 | 151.6 | 904.8 |
|  | 12 | 1188.79 | 331.74 | 426.88 | 333.01 | 217.84 | 1510.1 |
|  | 15 | 2040.38 | 443.36 | 450.76 | 450.76 | 391.22 | 2223.65 |
|  | 19 | 2851.36 | 773.88 | 989.52 | 737.22 | 287.96 | 4587.2 |
|  | 21 | 3876.85 | 1022.48 | 1220.44 | 976.75 | 490.76 | 3279.72 |

In this Example, MB49 cells, which exhibit very high cell growth rates, were intradermally administered, with a focus on whether or not eradication occurs in tumors of considerable size having a tumor diameter of 7-8 mm.

As a result, a tumor suppressing effect was observed with ADM alone, but eradication was not observed.

On the other hand, tumor eradication was observed in one of the three animals in the ADM 100 µg+HVJ-E 5000 HAU administration group.

Hence, the results demonstrated an antitumor effect of HVJ-E and ADM on MB49 cells.

Example 3

Adriamycin (ADM) Sensitivity of MB49 (Transitional Epithelial Cancer) Cells (Method)

The survival rate of MB49 cells, which depends on adriamycin (ADM) concentration, was examined by the method described below using WST-8 assay (cell counting kit-8; Dojindo Laboratories).

Adriamycin (trade name; Adriacin Injection, Kyowa Hakko Kogyo Co., Ltd.) was added to 10,000 MB49 cells, and the cells were prepared as 200 µl of sample solution and sown to a 96-well plate.

After 48 hours of cultivation, the supernatant was removed by WST-8 assay, 100 µl of a cell counting kit solution, previously diluted 10 fold with RPMI medium, was added, and the plate was allowed to stand at 37° C. for 1.5 hours. Absorbance at 450 nm was determined using a microplate reader. Assuming the absorbance of a sample of MB49 cells only to be 100% survival rate, the survival rates at various concentrations were calculated. Concentrations that produced survival rates of 50% and 90% were calculated and designated as $LD_{50}$ and $LD_{90}$.

(Results)

| | ADM (μg/ml) | | | | | |
|---|---|---|---|---|---|---|
| | 0.002 | 0.004 | 0.008 | 0.016 | 0.032 | 0.063 |
| survival rate (%) | 68.9 | 60.1 | 54 | 48 | 47.4 | 34.9 |

| | ADM (μg/ml) | | | | |
|---|---|---|---|---|---|
| | 0.125 | 0.25 | 0.5 | 1 | 2 |
| survival rate (%) | 27.6 | 22.6 | 17.2 | 11.7 | 6.7 |

Figure 12:
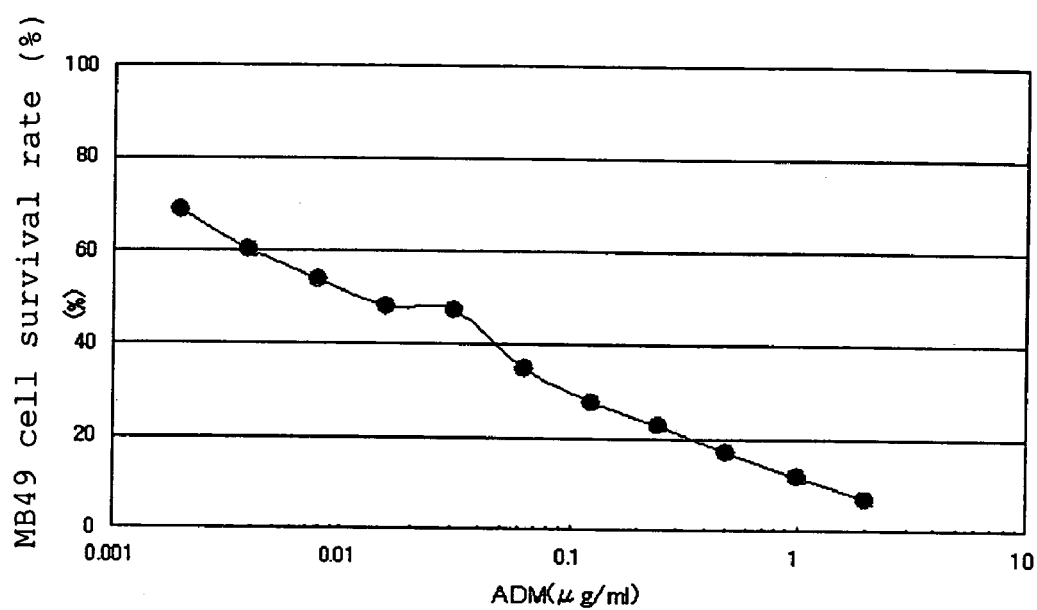
FIG. 12 is a graph showing the adriamycin sensitivity of MB49 cells.

The $LD_{50}$ concentration of ADM for MB49 cells was determined to be 0.008 μg/ml and the $LD_{90}$ concentration was determined to be 1 μg/ml (see FIG. 12).

From this result, it was shown that in the concurrent administration of MB49 cells, HVJ-E, and ADM into the bladder, the ADM sensitivity of MB49 cells could be reflected by an in vitro system.

Example 4

Antitumor effect of concurrent administration of MB49 cells, HVJ-E, and ADM into the bladder (Method)

Three 6-week-old female C57BL/6Cr Slc mice per group were anesthetized by administering a mixture of 90 μl of ketamine (50 mg) and 10 μl of xylazine (2% solution) to the left femoral muscle, a 24G catheter was inserted into the bladder, 100 μl of each of the following sample solutions was administered using a 1-ml syringe, and the catheter was indwelled for 1 hour.

The groups established are as follows:
1: MB49+ADM (0.008 μg/ml)
2: MB49+ADM (0.008 μg/ml)+HVJ-E (5000 HAU)
3: MB49+ADM (1 μg/ml)
4: MB49+ADM (1 μg/ml)+HVJ-E (5000 HAU)

The number of MB49 cells administered was $5 \times 10^6$ cells. After adjustment to a final volume of 100 μl, each solution was administered into the bladder. Two weeks later, the bladder was extirpated, and sections were prepared and stained with HE.

(Results)

Figure 13:
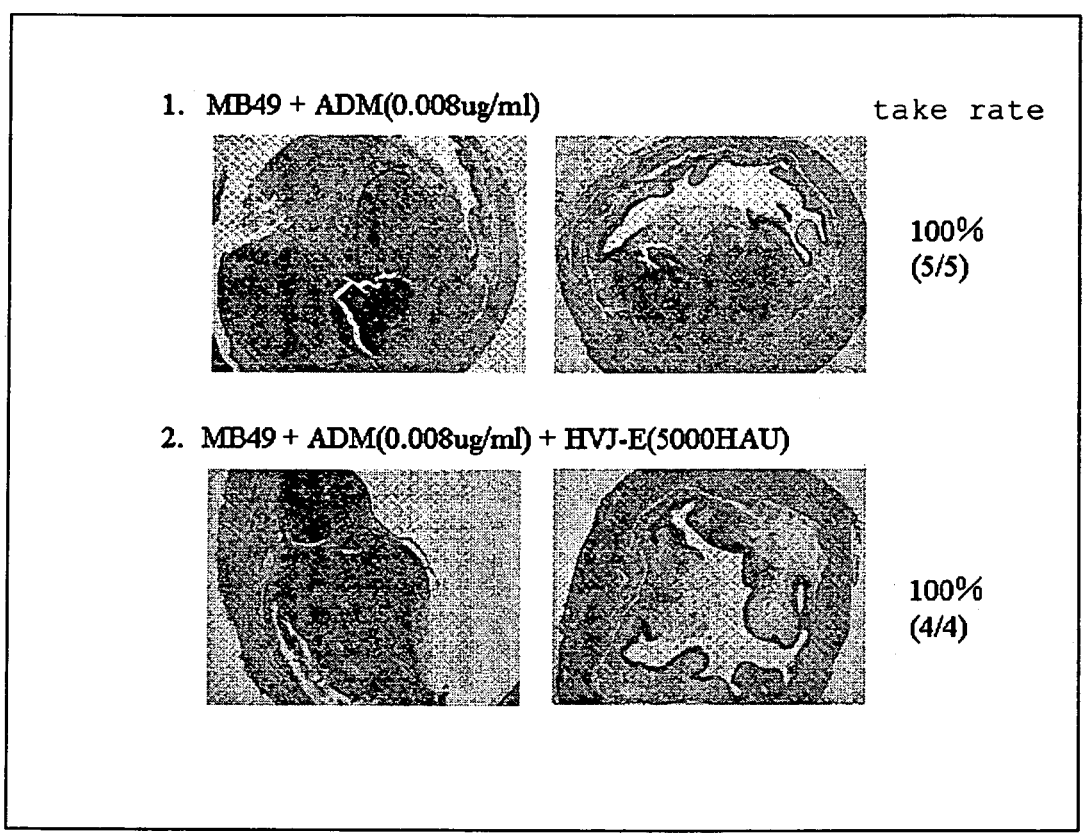
FIG. 13 is photomicrographs showing infiltration of MB49 cells into the bladder (Group 1 and Group 2, magnification rate ×400).
Figure 14:
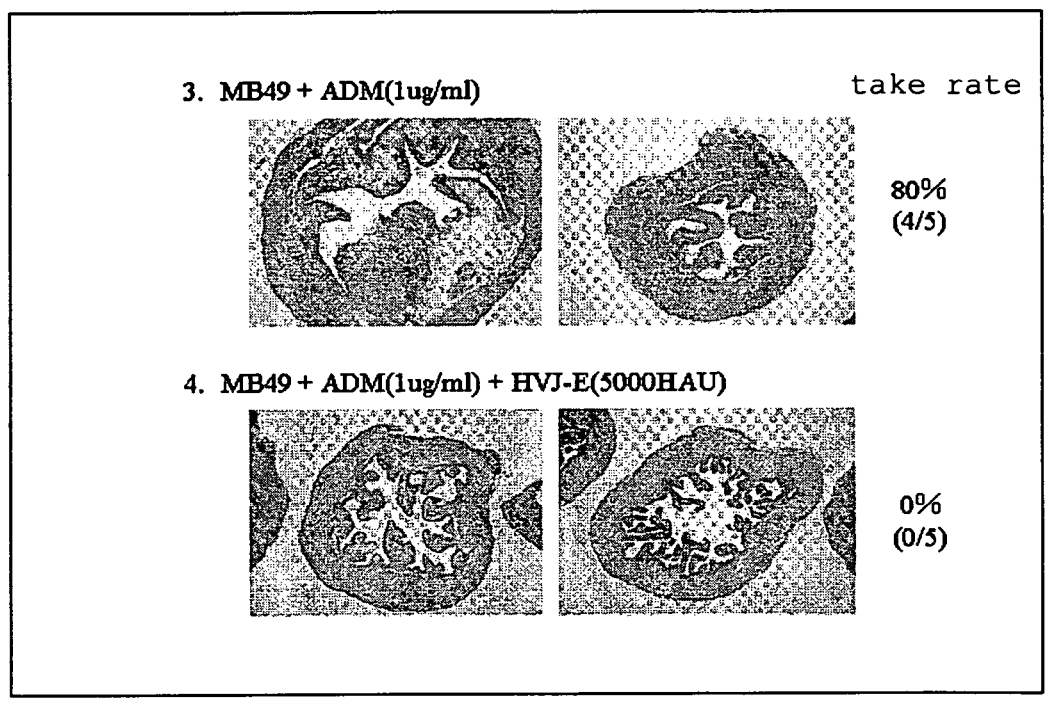
FIG. 14 is photomicrographs showing infiltration of MB49 cells into the bladder (Group 3 and Group 4, magnification rate ×400).
Figure 15:
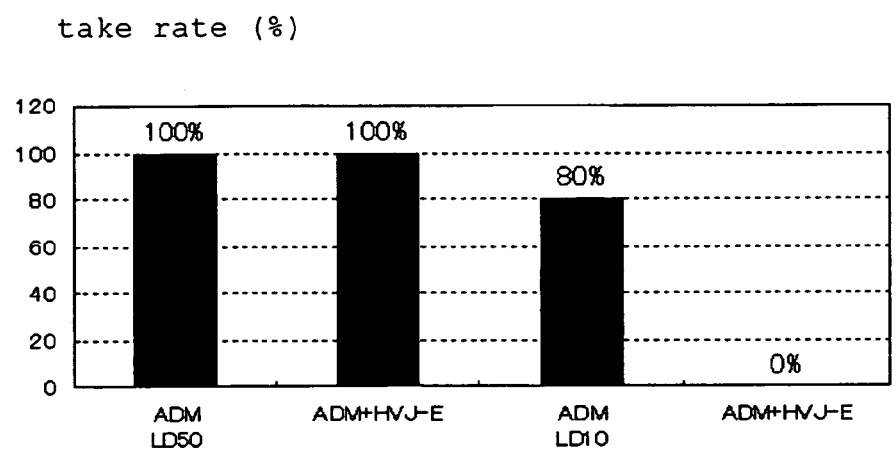
FIG. 15 is a graph comparing the MB49 take rate in the bladder (cancer incidence rate) among different groups.

Tumor infiltration was evaluated from images of HE staining. In Group 1 and Group 2, all animals showed evidence of infiltration of MB49 cells (see FIGS. 13 and 15). In FIG. 13, the densely purple (black) portion at the center indicates cancer cells. Even in Group 3, in which the ADM concentration was raised and a dose equivalent to the $LD_{90}$ was administered, infiltration of MB49 cells could not be prevented in 80% of the animals. However, in the group receiving the same regimen as Group 4, but supplemented with 5000 HAU HVJ-E, there were no animals having infiltration of MB49 cells (0/5, infiltration prevention rate 100%) (see FIGS. 14 and 15).

Hence, it was shown that infiltration of MB49 cells in the bladder could not be prevented with ADM alone but could be prevented using ADM and HVJ-E in combination.

In particular, in the group receiving HVJ-E in combination with ADM (1 μg/ml), the MB49 take rate in the bladder (cancer incidence rate) was remarkably suppressed compared with the group supplemented with ADM alone.

Example 5

Antitumor Effect of Cisplatin (CDDP) and HVJ-E in Combination (Method)

CT-26 mouse colon cancer cells were intradermally inoculated into the backs of BALB/c mice at $5 \times 10^6$ cells/head. Five days after the inoculation, treatment with HVJ-E and CDDP was started in the following animal groups. For each animal group, tumor volume was calculated as major diameter×minor diameter×minor diameter/2.

Animal Group:
1: Physiological saline group
2: HVJ-E alone
3: CDDP 1 mg/kg
4: CDDP 3 mg/kg
5: CDDP 1 mg/kg+HVJ-E (5,000 HAU)
6: CDDP 3 mg/kg+HVJ-E (5,000 HAU)
(n=5 or 6 for each group)

(Results)

Figure 16:
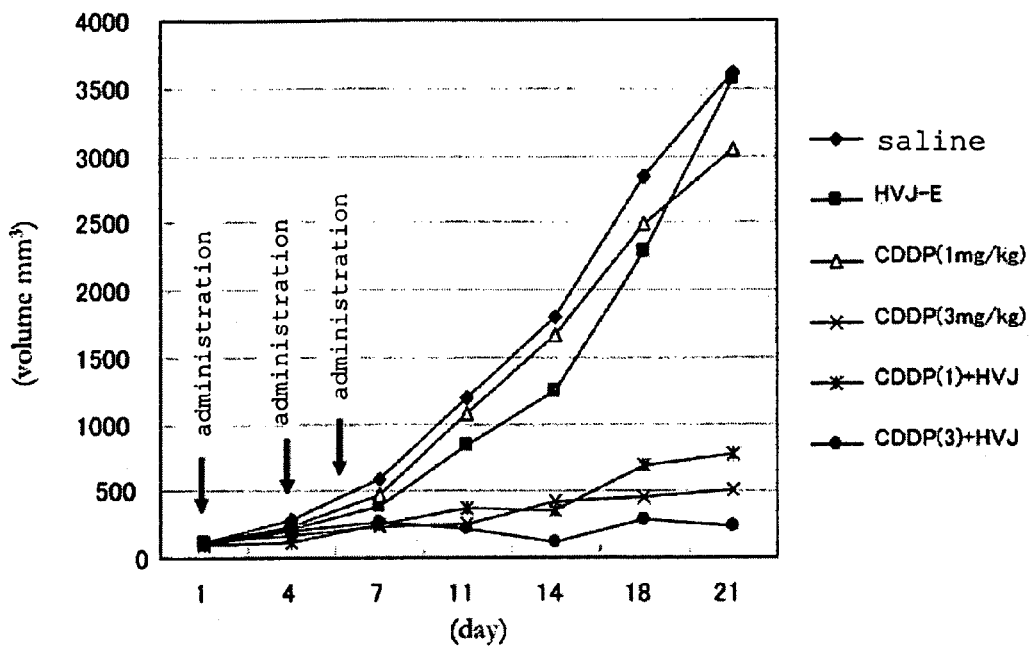
FIG. 16 is a graph showing the antitumor effects of a combination of CDDP and HVJ-E (egg-derived).
Figure 17:
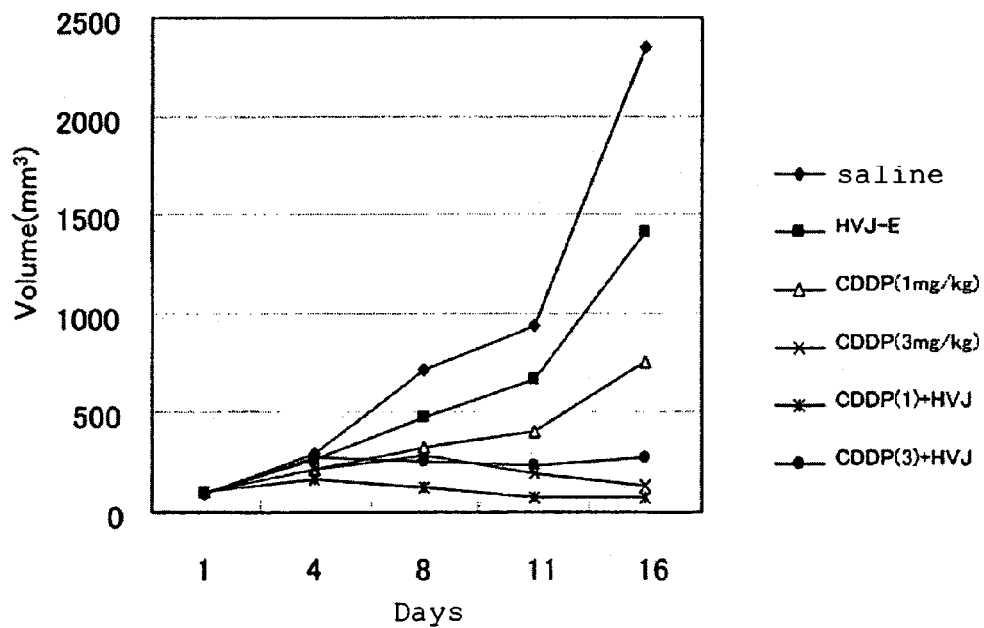
FIG. 17 is a graph showing the antitumor effects of a combination of CDDP and HVJ-E (cell-derived).

The mean values of tumor volume for individual groups tested using egg- and cell-derived HVJ-E are shown in FIG. 16 (egg-derived) and FIG. 17 (cell-derived). Regarding tumor volume, no major difference was observed among the three groups: physiological saline group, HVJ-E-alone administration group, and CDDP 1 mg/kg administration group [FIG. 16 (egg-derived)]. In the cell-derived HVJ-E administration group, the regression effect was greater in the order of the physiological saline group, HVJ-E-alone administration group, and CDDP 1 mg/kg administration group.

The tumor regression effect to note in this study was observed in 33-40% of the animals in the CDDP 1 mg/kg+ HVJ-E 5,000 HAU administration group and the CDDP 3 mg/kg+HVJ-E 5,000 HAU administration group (in both egg- and cell-derived HVJ-E). Hence, it was confirmed that an antitumor effect was obtained only when an anticancer drug was simply mixed with HVJ-E without being encapsulated therein.

Example 5

Responses of HVJ-E and HVJ to Mouse Dendritic Cells (DC)

(Method)

Recovery of Dendritic Cells (DC) from Mouse

The femurs and tibias of both lower limbs of a mouse were collected. Muscles and fats associated with the bones were removed to the maximum possible extent. Both ends of each bone were cut off. Serum-free medium (RPMI1640, containing antibiotics) was injected from the opening using a syringe with a 27 G needle to purge out the bone marrow by pressure. A sample solution containing the myelocytes recovered by the treatment was passed through a cell strainer having a pore diameter of 40 μm (BD Falcon Company), and the debris was removed. Centrifugation was performed at 1,500 rpm for 5 minutes, and the cells were recovered. The cells were suspended in DC medium [PRMI1640, 10% FCS (MBL, EQITECH Company), 10 ng/500 ml GMCSF (R&D System Company), 2 µl/500 ml 2-mercaptoethanol] (hereinafter DC medium). All the cells were counted, DC medium was added to obtain a cell density of $1 \times 10^6$ cells/ml, and the cells were sown to a 24-well plate at 1 ml per well. Two and four days later, the supernatant was exchanged with a fresh supply. The floating cells were recovered 6 days later.

Co-Cultivation of DC and HVJ or HVJ-E

The amount of cytokines induced by co-cultivation of DC and the live virus HVJ or inactivated HVJ-E was measured. HVJ or HVJ-E was added to the culture broth so that the m.o.i. relative to the DC ($1 \times 10^6$ cells/ml) would be 20. Effects on the presence or absence of N-tosyl-L-phenylalanine chloromethylketone (TPCK, 15 µM, Wako Pure Chemical Industries), which is an inhibitor of NF-KB, was also evaluated. Furthermore, the effect of the *Escherichia coli* cell wall (lipopolusaccaride, LPS, 10 µM), which is a typical Th1 immunity induing substance, was also evaluated. Cultivation was performed for 2 days, and the supernatant was recovered. The concentrations of the cytokines IL-12, IL-6, IL-5 and IL-4 in the solution were determined using an ELISA Development kit from R&D system Company.

Furthermore, DC maturation was also evaluated.

(Results)

Figure 18A:
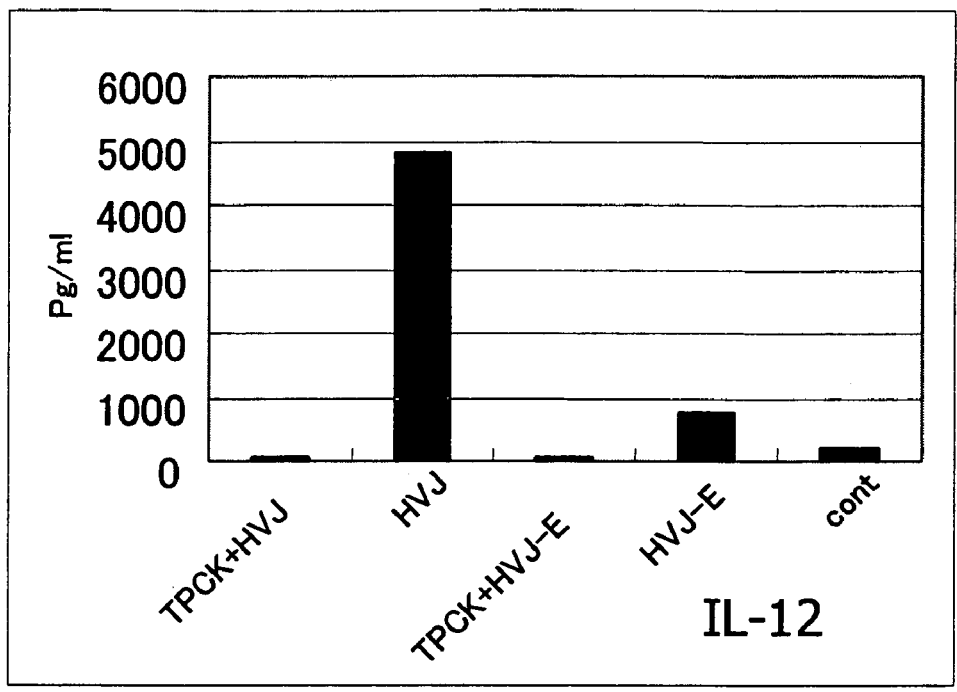
FIG. 18a is a graph showing immunity-inducting action for IL-12.
Figure 18B:
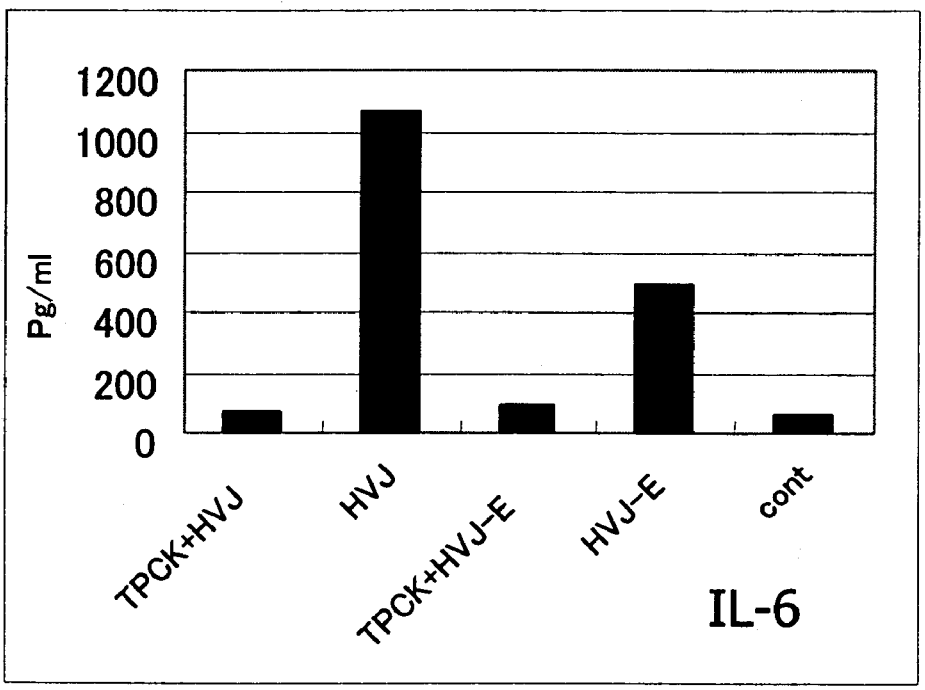
FIG. 18b shows immunity-inducting action for IL-6.
Figure 18C:
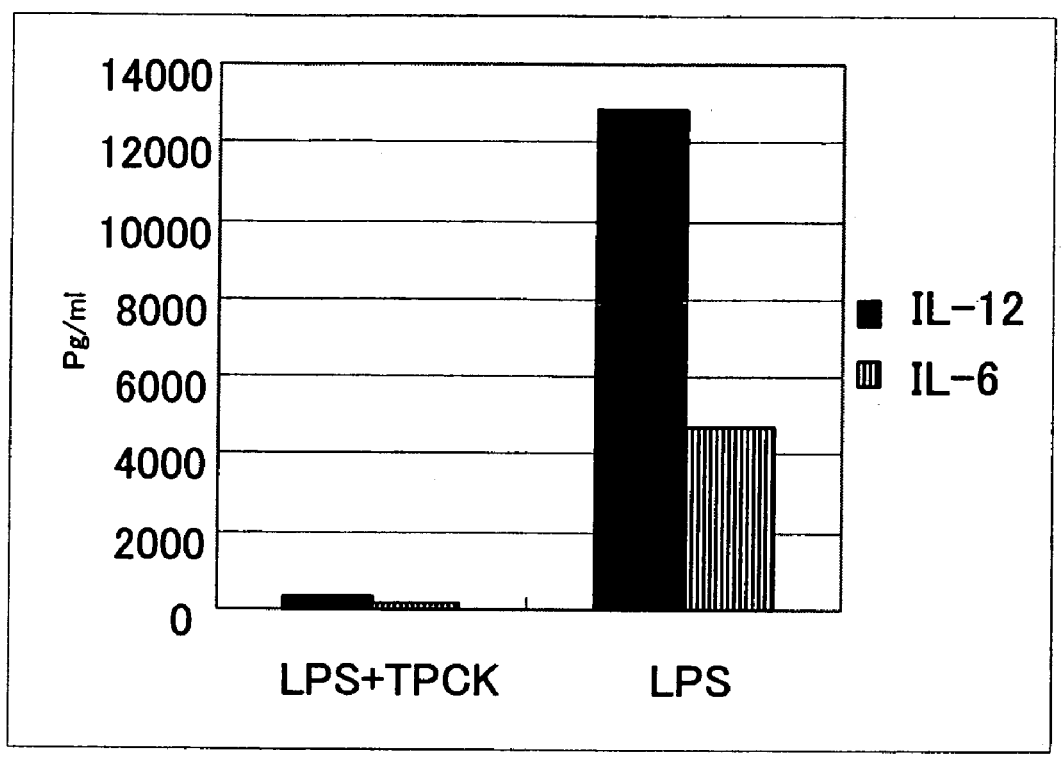
FIG. 18c is a graph comparing immunity-inducing actions for IL-6 and IL-12.

The results are shown in FIG. 18. Comparing HVJ and HVJ-E, the amount of IL-12 induced decreased considerably, from 4928 pg/ml with HVJ stimulation to 748 pg/ml with HVJ-E stimulation. On the other hand, the amount of IL-6 induced was 1066 pg/ml with HVJ stimulation and 496 pg/ml with HVJ-E stimulation. For IL-4 and -5, almost no induction was observed. (FIG. 18)

Stimulation with HVJ-E and HVJ induced DC maturation to an extent comparable to that obtained by stimulation with LPS.

Example 6

Effects of HVE-J on Regulatory T Cells (Reg T)

(Method)

CT-26 ($1 \times 10^5$ cells) was sown to a 96-well plate in a volume of 200 µl (DMEM, 10% FCS contained). On the following day, dendritic cells ($1 \times 10^5$ cells) were added. The medium was exchanged with 200 µl of DC medium. At that time, HVJ-E was added or not ($10^4$-$10^9$/well), and CDDP (1 µg/ml or 3 µg/ml) was also added. On the following day, $5 \times 10^5$ splenocytes recovered from BALB/c mouse were added. Cultivation was performed for 3 days. The cells were recovered, and T cells and regulatory T cells (reg T) were analyzed for BrdU uptake ratio by FACS.

(Results)

Figure 19:
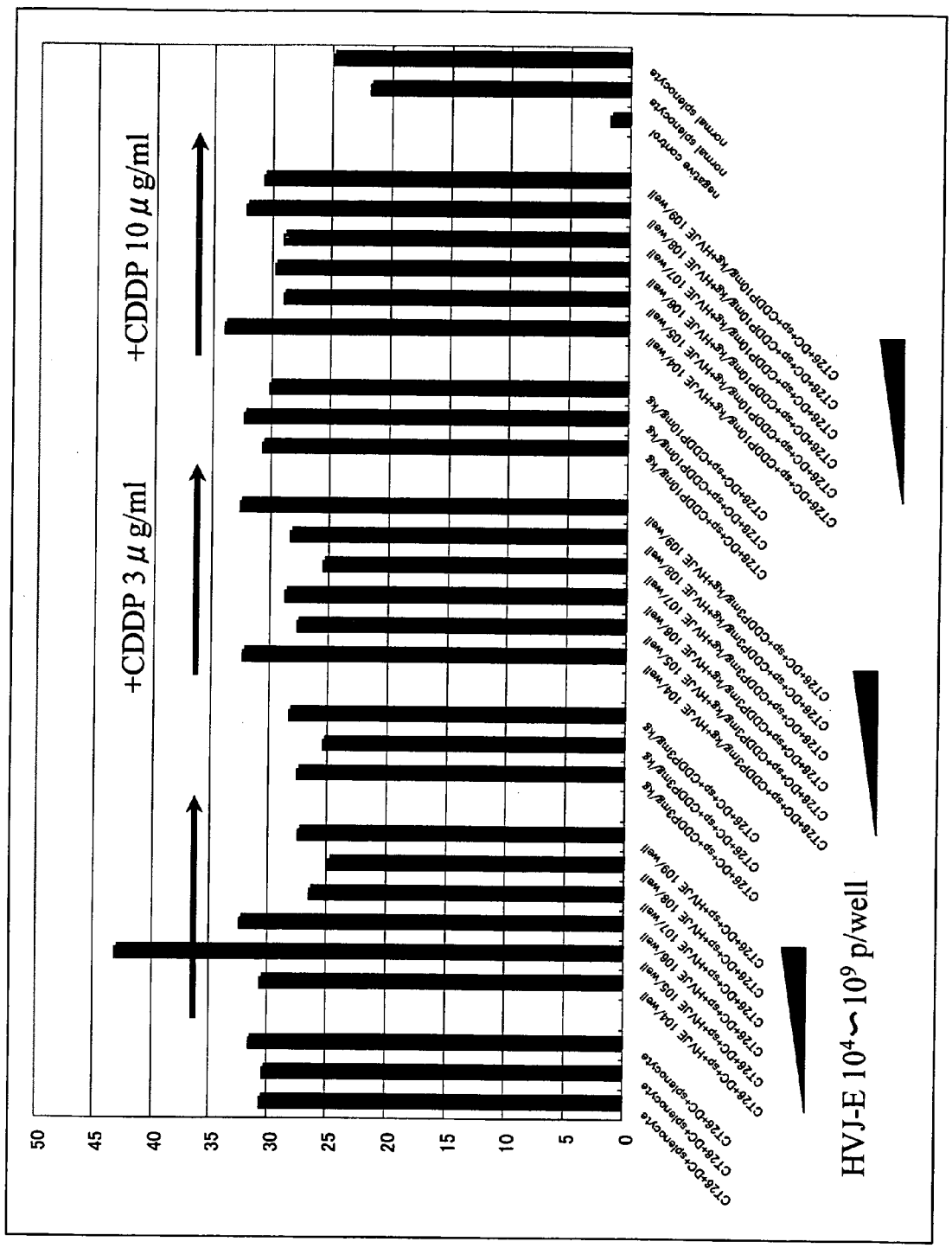
FIG. 19 is a graph showing increases and decreases in CD4+ cells.
Figure 20:
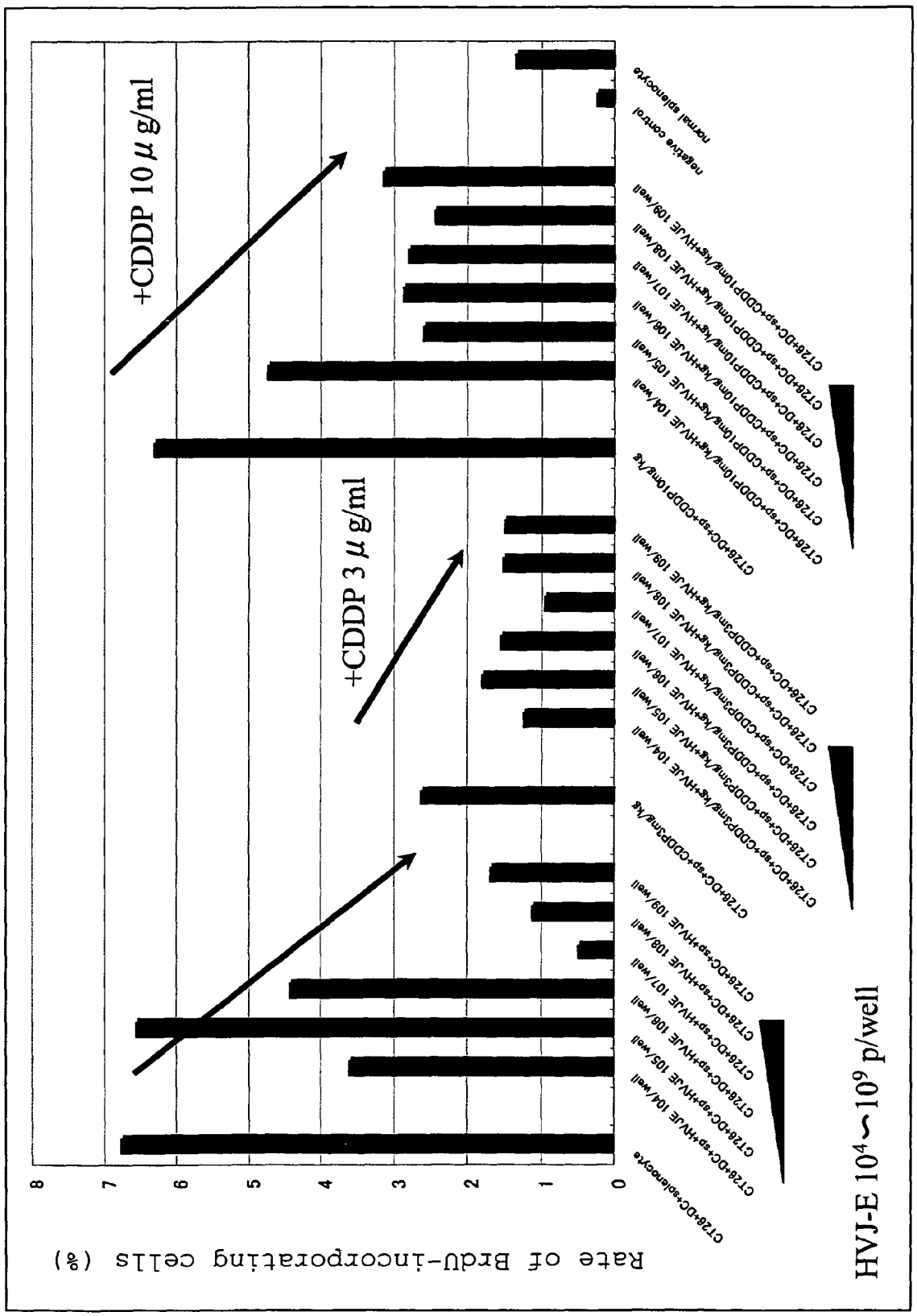
FIG. 20 is a graph comparing increases and decreases in regulatory T cells (CD4+CD25+).

When HVJ-E, HVJ-E+CDDP (1 µg/ml), and HVJ-E+CDDP (3 µg/ml) were allowed to act, the cell growth of T cells as a whole was not influenced but the cell growth of regulatory T cells (reg T) was suppressed HVJ-E-concentration-dependently. (FIGS. 19 and 20)

INDUSTRIAL APPLICABILITY

Embodying the present invention enables a new chemotherapy using an HVJ-E vector for all solid cancers rapidly increasing in Japan, such as lung cancer, breast cancer, digestive cancers such as stomach cancer, colon cancer, and esophagus cancer, head and neck cancers (maxillary cancer, tongue cancer, lip cancer, pharynx cancer, larynx cancer, mouth cancer and the like), gynecological cancers (uterine cancer, ovarian cancer, uterine cervix cancer and the like), urological cancers (prostate cancer, bladder cancer, kidney cancer, renal pelvic and ureteral cancer, testicular tumor, adrenal tumor, penis cancer and the like), osteochondrosarcoma, malignant lymphoma, cancer unknown primary, and the like. Accordingly, the present invention provides a pharmaceutical composition comprising a chemotherapeutic encapsulated in a viral vector that induces antitumor immunity, whereby various cancers can be treated, while increasing antitumor immunity in a living organism, and suppressing side-effects to normal cells.

Also, a pharmaceutical composition comprising HVE-J and an anticancer drug, which is another embodiment of the present invention, particularly enables efficient treatment for urological cancer.

This application is based on patent application Nos. 2004-108599, 2004-136756 and 2005-044639 filed in Japan, the contents of which are incorporated in full herein by this reference.

The invention claimed is:

1. A method for inhibiting tumor cell growth in an animal, comprising administering to said animal an effective amount of a composition consisting of a hemagglutinating virus of Japan envelope (HVJ-E) and a pharmaceutically acceptable carrier, wherein the composition is administered intratumorally.

2. The method of claim 1 wherein IL-12 and IL-6 in dendritic cells are induced or regulatory T cells are inhibited.

* * * * *